US012807725B2

(12) United States Patent
Qiu et al.

(10) Patent No.: US 12,807,725 B2
(45) Date of Patent: Nov. 24, 2026

(54) ANTI-GITR MONOCLONAL ANTIBODY AND MEDICAL USE THEREOF

(71) Applicant: INNOLAKE BIOPHARMA (HANGZHOU) CO., LTD., Zhejiang (CN)

(72) Inventors: Junzhuan Qiu, Taicang (CN); Zhensheng Wang, Taicang (CN); Kai Sun, Taicang (CN); Man Zhou, Taicang (CN); Junyong Chen, Taicang (CN); Jian Sun, Taicang (CN); Rishan Ou, Taicang (CN)

(73) Assignee: INNOLAKE BIOPHARMA (HANGZHOU) CO., LTD., Zhejiang (CN)

( * ) Notice: Subject to any disclaimer, the term of this patent is extended or adjusted under 35 U.S.C. 154(b) by 849 days.

(21) Appl. No.: 18/013,504

(22) PCT Filed: Mar. 16, 2021

(86) PCT No.: PCT/CN2021/080981
§ 371 (c)(1),
(2) Date: Dec. 28, 2022

(87) PCT Pub. No.: WO2022/001189
PCT Pub. Date: Jan. 6, 2022

(65) Prior Publication Data

US 2023/0295323 A1 Sep. 21, 2023

(30) Foreign Application Priority Data

Jun. 28, 2020 (CN) ......................... 202010597133.7

(51) Int. Cl.
*A61K 39/395* (2006.01)
*A61P 35/00* (2006.01)
*C07K 16/28* (2006.01)

(52) U.S. Cl.
CPC .......... *C07K 16/2878* (2013.01); *A61P 35/00* (2018.01); *C07K 2317/24* (2013.01); *C07K 2317/565* (2013.01)

(58) Field of Classification Search
None
See application file for complete search history.

(56) References Cited

U.S. PATENT DOCUMENTS

2022/0119541 A1* 4/2022 Qi ........................... A61P 31/00

FOREIGN PATENT DOCUMENTS

CN 101218257 7/2008
CN 109641967 4/2019
CN 110386981 10/2019
(Continued)

OTHER PUBLICATIONS

De Araújo-Souza et al., Differential interferon-γ production by naive and memory-like CD8 T cells, J. Leukoc. Biol. ;108:1329-1337, 2020.*

(Continued)

*Primary Examiner* — Claire Kaufman
(74) *Attorney, Agent, or Firm* — Nixon & Vanderhye, PC

(57) ABSTRACT

Provided are an anti-GITR monoclonal antibody and a humanized antibody thereof, which can be used to prepare a drug used for activating immune response, particularly a related drug for treating cancer.

8 Claims, 4 Drawing Sheets

Specification includes a Sequence Listing.

| ng/ml | h10E11(AV)-hIgG1 | h10E11(AV)-hIgG1(3A) | h10E11(AV)-hIgG4 | h4E4-hIgG1 | h4B11-hIgG1 | h3F5-hIgG1 |
|---|---|---|---|---|---|---|
| IC50 | 140.0 | 150.8 | 223.0 | 168.8 | 263.9 | 101.1 |

(56) References Cited

FOREIGN PATENT DOCUMENTS

| | | | |
|---|---|---|---|
| CN | 110431152 | | 11/2019 |
| CN | 110461874 | | 11/2019 |
| CN | 110903392 | | 3/2020 |
| CN | 111234018 | | 6/2020 |
| CN | 111732658 | | 10/2020 |
| WO | 2015187835 | A2 | 12/2015 |
| WO | 2017156058 | A1 | 9/2017 |
| WO | 2018158658 | A1 | 9/2018 |

OTHER PUBLICATIONS

Whitmire et al.,Interferon-γ acts directly on CD8 +T cells to , J. Exp. Med. 201(7):1053-159, 2005.*

Tian et al., The Role of GITR/GITRL Interaction in Autoimmune Diseases, Front. Immunol. 11:588682, 7 pages, Oct. 8, 2020.*

International Search Report dated Jun. 21, 2021, for PCT/CN2021/080981, 11 pp.

Written Opinion of the ISA dated Jun. 21, 2021, for PCT/CN2021/080981, 11 pp.

Chinese First Office Action dated Jul. 21, 2021, for CN202010597133.7, 12 pp.

* cited by examiner

| ng/ml | h10E11(AV)-hIgG1(3A) | h10E11(AV)-hIgG4 | h4E4-hIgG1 | h4B11-hIgG1 | h3F5-hIgG1 |
|---|---|---|---|---|---|
| EC50 | 6.556 | 19.88 | 50.43 | 4.769 | 22.64 |

| ng/ml | h10E11(AV)-hIgG1 | h10E11(AV)-hIgG1(3A) | h10E11(AV)-hIgG4 | h4E4-hIgG1 | h4B11-hIgG1 | h3F5-hIgG1 |
|---|---|---|---|---|---|---|
| EC50 | 50.91 | 102.2 | 94.36 | 89.54 | 132.2 | 111.5 |

| ng/ml | h10E11(AV)-hIgG1 | h10E11(AV)-hIgG1(3A) | h10E11(AV)-hIgG4 | h4E4-hIgG1 | h4B11-hIgG1 | h3F5-hIgG1 |
|---|---|---|---|---|---|---|
| IC50 | 140.0 | 150.8 | 223.0 | 168.8 | 283.9 | 101.1 |

ANTI-GITR MONOCLONAL ANTIBODY AND MEDICAL USE THEREOF

CROSS-REFERENCE TO RELATED APPLICATIONS

This application is the U.S. national phase of International Application No. PCT/CN2021/080981 filed Mar. 16, 2021, which designated the U.S. and claims priority to CN patent application No. 202010597133.7 filed Jun. 28, 2020, the entire contents of each of which are hereby incorporated by reference.

REFERENCE TO SEQUENCE LISTING SUBMITTED ELECTRONICALLY

The content of the electronically submitted sequence listing (Name: 6492_0069_Sequence_Listing.txt; Size: 90,164 bytes; and Date of Creation: May 26, 2023) filed on May 26, 2023 is incorporated herein by reference in its entirety.

TECHNICAL FIELD

The present disclosure pertains to the field of tumor and immunology drugs, and in particular, relates to an anti-GITR monoclonal antibody and medical use thereof.

BACKGROUND

GITR is a glucocorticoid-induced TNFR-related protein, also known as TNFRSF18 or CD357, and is a type I transmembrane protein highly expressed in Treg cells and lowly expressed in naive and memory T cells [Shimizu et al., (2002), Nat. Immunol. 3:135-42; Nocentini et al., (2009), Adv. Exp. Med. Biol. 647:156-73; McHughet et al., (2002), Immunity 16:311-23; Nocentini et al., (2005), Eur J Immunol 35:1016-1022]. After being activated, naive T cells and Treg cells rapidly up-regulate the expression of GITR (Shimizu et al., (2002), Nat. Immunol. 3:135-42; Krausz et al., (2007, Scientific World Journal 7:533-66)). There is also low to moderate expression of GITR in activated innate immune cells such as natural killer cells, macrophages and dendritic cells (DCs) [Clouthier et al., (2014), Growth Factor Rev. 25:91-106]. GITR ligands (GITRLs) are type II transmembrane proteins belonging to the TNF superfamily, a certain amount of which are found expressed on the surfaces of endothelial cells including B cells, macrophages and dendritic cells (DCs)), as well as activated antigen-presenting cells (APCs) [Yu et al., (2003), Biochem. Biophys. Res. Commun.310:433-438; Toneet et al., (2003), Proc. Natl. Acad. Sci. USA 100:15059-15064].

Through the interaction between GITRL or GITR agonist antibodies and GITR, GITR can be stimulated to enhance TCR-induced T cell proliferation and cytokine production [Ronchetti et al., (2004), Eur. J. Immunol. 34:613-622; Tone et al., (2003), Proc. Natl. Acad. Sci. USA 100:15059-15064; Stephens et al., (2004), J. Immunol. 173:5008-5020], and reduce sensitivity of effector T cells to Treg cell-mediated immunosuppression [Ronchetti et al., (2007), Eur. J. Immunol. 37:1165-1169; Stephens et al., (2004), J. Immunol. 173:5008-5020]. Activation of GITR may recruit TNFR-associated factors 2 (TRAF 2) and 5 (TRAF5), and induce activation of transcription factor NF-κB and MAP kinase-induced signaling pathways [Snellet et al., (2011), Immunol. Rev. 244:197-217; Snell et al., (2010), J. Immunol. 185: 7223-34], and induce transcription of anti-apoptotic Bcl-XL proteins, thereby reducing T cell apoptosis caused by cell activation [Ronchetti et al., (2004), Eur. J. Immunol. 34:613-622; Esparza et al., (2006), J. Biol. Chem. 281:8555-64]. The activation of GITR can further lead to activation of NFkB-dependent TRAF6 and production of IL-9, thereby enhancing the function of DC cells and activating the cytotoxic response of T lymphocytes [Kim et al., (2015), Nat. Med. 21:1010-7]. GITR signaling can also promote degradation of FoxP3 [Cohenet et al., (2010), PLOS ONE 5:10436; Schaer et al., (2013), Cancer Immunology Research 1:320-331] and phosphorylation of c-Jun N-terminal kinase (JNK) [Joetham et al., (2012), J Biol. Chem. 287:17100-17108], thereby further inhibiting the immune suppression function of Treg cells. In addition, it has also been reported that anti-GITR antibodies can reverse the inhibitory effect of Treg cells on B cell-mediated antibody production [Cava et al., (2004), J. Immunol. 173:3542-3548].

Preclinical studies have shown that activation of the GITR signaling pathway can significantly enhance elimination of tumors. The effect depends on activation of immune effector cells [Ramirez et al., (2006), J Immunol 176:6434-6442; Boczkowski et al., (2009), Cancer Gene Ther. 16:900-911; Mitsui et al., (2010), Clin. Cancer Res. 16:2781-91], and also depends on removal or inhibition of the immunosuppression activity of Treg cells [Cohen et al., (2010), PLOS ONE 5: e10436; Coe et al., (2010), Cancer Immunol. Immunother. 59:1367-77; Xiao et al., (2015), Nat. Commun. 6:8266]. When GITR activating antibodies are used alone, fewer Treg cells may enter tumor tissues, and foxp3 is not expressed in Treg cells in the tumor, thereby locally eliminating the immunosuppressive effect of Treg cells in the tumor. Ultimately, the Teff/Treg cell ratio is increased in the tumor microenvironment, and the activity and function of Teff cells are enhanced (Cohen et al., (2010), PLOS ONE 5: e10436). In an ovarian cancer model, the combination of anti-GITR and anti-PD-1 antibodies could improve patient survival overall; and after 90 days of treatment, up to 20% of mice were tumor-free. After analyses of the results of leukocytes (TILs) entering tumors in mice, it was found that the number of CD4+ and CD8+ effector memory T cells was significantly increased, while the number of Treg immune regulatory cells was significantly reduced [Lu et al., (2014), J. Transl. Med. 12:36-47]. Although monotherapy was not significantly effective with GITR antibodies, their combination with anti-CTLA4 antibodies showed a significantly enhanced synergistic antitumor effect in MethA and CT26 tumor models [Ko et al., (2005), J. Exp. Med. 202:885-91; Mitsui et al., (2010), Clin. Cancer Res. 16:2781-91].

SUMMARY

In view of this, in the present disclosure, an anti-GITR monoclonal antibody, which has excellent effect of activating the activities of GITR and immune cell and blocking the interaction between GITR-L and GITR, is obtained through hybridoma technology; and the antibody is successfully humanized. The antibody has prominent application potential in the preparation of medications for stimulating and improving immune responses as well as medications for treating cancer.

The present disclosure provides an anti-GITR monoclonal antibody or an antigen-binding fragment thereof, which comprises a heavy chain and a light chain, where an amino acid sequence of CDR1 of the heavy chain is selected from the group consisting of SEQ ID NOs: 2, 10, 18, 26, 34, 42, 50, 58, 66, 74, 82, 90, 98 and 106; an amino acid sequence of CDR2 of the heavy chain is selected from the group consisting of SEQ ID NOs: 3, 11, 19, 27, 35, 43, 51, 59, 67, 75, 83, 91, 99 and 107; an amino acid sequence of CDR3 of the heavy chain is selected from the group consisting of SEQ ID NOs: 4, 12, 20, 28, 36, 44, 52, 60, 68, 76, 84, 92, 100 and 108; an amino acid sequence of CDR1 of the light chain is selected from the group consisting of SEQ ID NOs: 6, 14, 22, 30, 38, 46, 54, 62, 70, 78, 86, 94, 102 and 110; an amino acid sequence of CDR2 of the light chain is selected from the group consisting of SEQ ID NOs: 7, 15, 23, 31, 39, 47, 55, 63, 71, 79, 87, 95, 103 and 111; and an amino acid sequence of CDR3 of the light chain is selected from the group consisting of SEQ ID NOs: 8, 16, 24, 32, 40, 48, 56, 64, 72, 80, 88, 96, 104 and 112, and wherein the heavy and light chains of the antigen-binding fragment comprise amino acid sequences spanning from CDR1 through CDR3 of the heavy and light chains of the antibody, respectively.

Further, in the anti-GITR monoclonal antibody or the antigen-binding fragment thereof according to the present disclosure, an amino acid sequence of a heavy chain variable region is selected from the group consisting of SEQ ID NOs: 1, 9, 17, 25, 33, 41, 49, 57, 65, 73, 81, 89, 97 and 105, and an amino acid sequence of a light chain variable region is selected from the group consisting of SEQ ID NOs: 5, 13, 21, 29, 37, 45, 53, 61, 69, 77, 85, 93, 101 and 109.

Further, the heavy chain and the light chain of the anti-GITR monoclonal antibody or the antigen-binding fragment thereof according to the present disclosure are humanized; and an amino acid sequence of a humanized heavy chain variable region is selected from the group consisting of SEQ ID NOs: 113, 115, 117 and 119; and an amino acid sequence of a humanized light chain variable region is selected from the group consisting of SEQ ID NOs: 114, 116, 118 and 120.

Further, in the humanized anti-GITR monoclonal antibody or antigen-binding fragment thereof according to the present disclosure, a full-length amino acid sequence of the humanized heavy chain is selected from the group consisting of SEQ ID NOS: 121, 123, 125, 127, 128, 129 and 130, and a full-length amino acid sequence of the humanized light chain is selected from the group consisting of SEQ ID NOs: 122, 124, 126 and 131.

Further, the present disclosure correspondingly discloses a nucleotide sequence encoding the above anti-GITR monoclonal antibody or the antigen-binding fragment thereof.

Further, the present disclosure discloses the above anti-GITR monoclonal antibody or the antigen-binding fragment thereof for use in preparation of: a medication for activating T lymphocytes, a medication for blocking binding of GITR-L to GITR, or a medication for increasing expression of IL-2 and IFN-γ in T lymphocytes.

Further, the present disclosure discloses a monoclonal antibody conjugate, comprising a monoclonal antibody and a conjugating part, where the monoclonal antibody is the anti-GITR monoclonal antibody or the antigen-binding fragment thereof according to the present disclosure, and the conjugating part is selected from one or more of a radionuclide, a medication, a toxin, a cytokine, a cytokine receptor fragment, an enzyme, fluorescein, and biotin.

Further, the present disclosure discloses the above monoclonal antibody conjugate for use in preparation of: a medication for activating T lymphocytes, a medication for blocking binding of GITR-L to GITR, or a medication for increasing expression of IL-2 and IFN-γ in T lymphocytes.

Further, the present disclosure discloses the above monoclonal antibody conjugate for use in preparation of a medication for preventing, treating, and/or assistantly treating a tumor.

The present disclosure has the following benefits: in the present disclosure, recombinant GITR prepared with a mammalian cell expression system is used as an antigen to immunize mice, and the spleen cells of the mice are fused with myeloma cells to obtain hybridoma cells. After multiple cloning and screening of a large number of the hybridoma cells, some monoclonal hybridoma cell lines are obtained. These hybridoma cell lines can produce monoclonal antibodies that specifically bind to GITR with high affinity, can promote the secretion of IL-2 and INF-γ in mixed lymphocyte reactions, and can effectively block the binding of GITR-L to GITR, and also can be used to construct humanized antibodies in a complementarity determinant grafting method by cloning genes encoding the light and heavy chain variable regions of the antibodies via RT-PCR. In vitro functional tests show that these humanized GITR antibodies can specifically bind to GITR proteins with high affinity, can significantly promote the secretion of cytokines IL-2 and INF-γ by T cells, and can block the binding of GITR-L to GITR. The test results show that the monoclonal antibody or the antigen-binding fragment thereof according to the present disclosure, or the monoclonal antibody conjugate comprising the monoclonal antibody or the antigen-binding fragment thereof according to the present disclosure has good application potential in preparation of medications for activating T lymphocytes, medications for increasing the expression of IL-2 and INF-γ in T lymphocytes, medications for blocking the binding of GITR-L to GITR, and medications for preventing, treating, and/or assistantly treating tumors.

DETAILED DESCRIPTION

Figure 1:
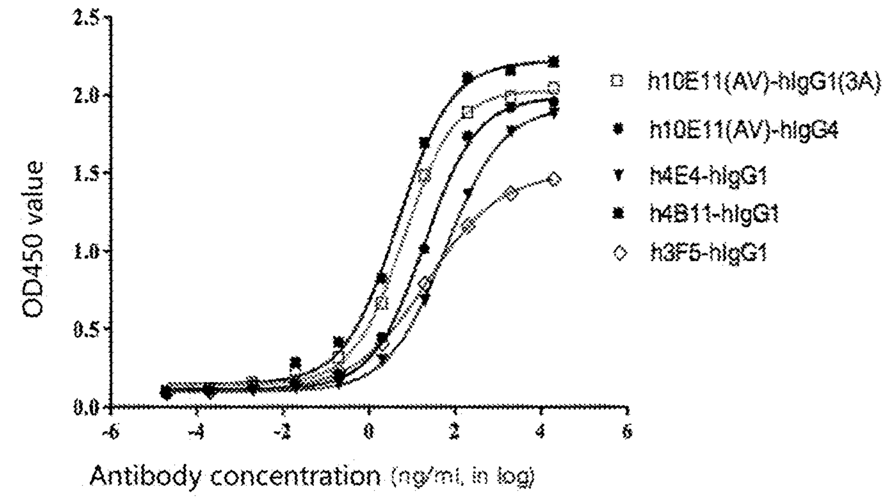
FIG. 1 shows EC50 for the binding of the humanized anti-GITR antibodies to GITR-mFc proteins detected in ELISA assay.

Technical solutions of the present disclosure are further described in the following embodiments. Persons skilled in the art should understand that the examples are only intended to help understand the present disclosure, and should not be construed as specific limitations on the present disclosure; the assays used in the following examples are all conventional methods unless otherwise specified; and materials, reagents and the like used in the following examples are all commercially available unless otherwise specified. Tables 1 to 3 show the amino acids of the antibodies involved in the present disclosure.

TABLE 1

Light Chain CDR Sequences of GITR Antibodies

| Name | LCDR | SEQ ID NO | Sequence |
|---|---|---|---|
| 4E1 | 1 | 6 | KSSQSLLDSDGKTYLN |
| | 2 | 7 | LVSELDS |
| | 3 | 8 | WQGTHFPWT |
| 8H4 | 1 | 14 | SASSSVSYMY |
| | 2 | 15 | DTSTLAS |
| | 3 | 16 | QQWSSFPPT |
| 4E4 | 1 | 22 | RSSQSIVYSNGNTYLN |
| | 2 | 23 | KVSNRFS |
| | 3 | 24 | FQGSHVPWT |
| 3F5 | 1 | 30 | KSSQSLLDRDGKTYLN |
| | 2 | 31 | LVSILDS |
| | 3 | 32 | WQGTHFPWT |
| 4C1 | 1 | 38 | RASENIYSNLA |
| | 2 | 39 | AATNLAD |
| | 3 | 40 | QHFWGPPWT |
| 7D7A2 | 1 | 46 | TASSSVSSSYFH |
| | 2 | 47 | STSNLAS |
| | 3 | 48 | HQYHHSPRT |
| 7E11 | 1 | 54 | RASENIYSNLA |
| | 2 | 55 | AATNLAD |
| | 3 | 56 | QHFWGPPWT |
| 10E11 | 1 | 62 | RASQSVNNYLH |
| | 2 | 63 | YASQSIS |
| | 3 | 64 | QQSNRWPLT |
| 3G12 | 1 | 70 | RASENIYSNLA |
| | 2 | 71 | AATNLAD |
| | 3 | 72 | QHFWGPPWT |
| 4B11 | 1 | 78 | RASQSVSTSTYSYVH |
| | 2 | 79 | YASNLES |
| | 3 | 80 | QHSWGNPWT |
| 5F1 | 1 | 86 | SASSSVSYMH |
| | 2 | 87 | STSNLAS |
| | 3 | 88 | HQRSGHTFT |
| 5F6 | 1 | 94 | RASQSVSTSSYSYMH |
| | 2 | 95 | YASNLES |
| | 3 | 96 | QHGWEIPYT |
| 13G12 | 1 | 102 | GASSSVSYMY |
| | 2 | 103 | DTFNLAS |
| | 3 | 104 | QHWSSYPPT |
| 9B3 | 1 | 110 | RASQSVNNYLH |
| | 2 | 111 | YVSQSIS |
| | 3 | 112 | QQSNRWPLT |

TABLE 2

Heavy Chain CDR Sequences of GITR Antibodies

| Name | HCDR | SEQ ID NO | Sequence |
|---|---|---|---|
| 4E1 | 1 | 2 | SDYAWN |
| | 2 | 3 | YIRNSGTTSYNPSLKS |
| | 3 | 4 | SGHHDLFDY |
| 8H4 | 1 | 10 | DYYMN |
| | 2 | 11 | NINPNHDYTSYNQKFKG |
| | 3 | 12 | YYYAMDY |
| 4E4 | 1 | 18 | DHYMN |
| | 2 | 19 | DIDPKNGGTLYNQNFKG |
| | 3 | 20 | REAMDY |
| 3F5 | 1 | 26 | DHYMH |
| | 2 | 27 | DINPNSGGTINNQNFKG |
| | 3 | 28 | GFSGLAY |
| 4C1 | 1 | 34 | SYWMQ |
| | 2 | 35 | TIYPGDGDTRYTQKFKG |
| | 3 | 36 | FEGRQFAY |
| 7D7A2 | 1 | 42 | RYWIE |
| | 2 | 43 | EILPGSGYNNSNDKFKG |
| | 3 | 44 | KGTFYTMDH |
| 7E11 | 1 | 50 | SYWMQ |
| | 2 | 51 | TIYPGDGDTRYTQKFKG |
| | 3 | 52 | FEGRQFAY |
| 10E11 | 1 | 58 | RYWIE |
| | 2 | 59 | EILPGSDYANYNEKFKG |
| | 3 | 60 | KGAYYALDF |
| 3G12 | 1 | 66 | SYWMQ |
| | 2 | 67 | TIYPGDGDTRYTQKFKG |
| | 3 | 68 | FYGGAMDS |
| 4B11 | 1 | 74 | DSVLH |
| | 2 | 75 | YIHPYNDDTKFHDSFKG |
| | 3 | 76 | NDELRVALDY |
| 5F1 | 1 | 82 | SDYAWN |
| | 2 | 83 | YITYSGSTGYNPSLKS |
| | 3 | 84 | DWPFAY |
| 5F6 | 1 | 90 | RYTMS |
| | 2 | 91 | YISNGGGSTYYPDTVKG |
| | 3 | 92 | AEAGTDWFAY |
| 13G12 | 1 | 98 | SNWMN |
| | 2 | 99 | NIYPSNGGTNYNEKFKS |
| | 3 | 100 | HSNYVGAMDY |
| 9B3 | 1 | 106 | RYWIE |
| | 2 | 107 | EILPGSDYANYNEKFKG |
| | 3 | 108 | KGAYYALDF |

TABLE 3

Light Chain and Heavy Chain Variable Region Sequences and Full-length Antibody Sequences of Antibodies

| Name | Region[1] | SEQ ID NO | Sequence |
|---|---|---|---|
| 4E1 (murine) | Light chain variable | 5 | DVVMTQTPLTLSFTIGQPASISCKSSQSLLDSDGKTYLNWLLQR PGQSPKRLIYLVSELDSGVPDRFTGSGSGTDFTLQISRVEAEDLG VYYCWQGTHFPWTFGGQTKLEIKRA |
| 4E1 (murine) | Heavy chain variable | 1 | DVQLQESGPGLVKPSQSLSLTCTVTGYSITSDYAWNWIRQFPG NKLEWMGYIRNSGTTSYNPSLKSRISITRDTSKNIIFFLQLNSVT TEDTATYYCTRSGHHIDLFDYWGQGTTLTVSS |
| 8H4 (murine) | Light chain variable | 13 | QIVLTQSPAIMSAFPGEKVTMTCSASSSVSYMYWYQQKPGSSP RLLIFDTSTLASGVPVRFSGSGSGTSHSLTISRMEAEDAATYYCQ QWSSFPPTFGAGTRLELKRA |
| 8H4 (murine) | Heavy chain variable | 9 | EVQLQQSGPELVRPGASVNISCKASGYTFTDYYMNWVKQSHG KSLEWIGNINPNHDYTSYNQKFKGKATLTVDKSSNTAYMELRS LTSEDSAVYYCARYYYAMDYWGQGTSVTVSS |
| 4E4 (murine) | Light chain variable | 21 | DVLMTQIPLSLPVSFGDQASISCRSSQSIVYSNGNTYLNWYLQK PGQSPKLLIYKVSNRFSGVPDRFSGSGSGTDFTLKISRVEAEDLG VYYCFQGSHVPWTFGGGTKLEIKRA |
| 4E4 (murine) | Heavy chain variable | 17 | EVQLQQSGPELVKPGASVKISCKASGYTFTDHYMNWVKQSHG KSLEWIGDIDPKNGGTLYNQNFKGRATLTVDKSSSTAYMDLRS LTSEDSAVYYCARREAMDYWGQGTSVTVSS |
| 3F5 (murine) | Liglit chain variable | 29 | DVVMTQTPLTLSVTIGQPASISCKSSQSLLDRDGKTYLNWLFQR PGQSLKRLIYLVSILDSGVPDRFTGSGSGTDFTLKISRVEAGDLG [YYCWQGTHFPWTFGGGTKLEIKRA |
| 3F5 (murine) | Heavy chain variable | 25 | EVQLQQSGPELVKPGTSVKISCKASGYTFTDHYMHWVRQSHG KSLEWIGDINPNSGGTINNQNFKGKATLTVDKSSNTAYMGLIIS LTSEDSAVYYCASGFSGLAYWGQGTLVTVSA |
| 4C1 (murine) | Light chain variable | 37 | MTQSPASLSVSVGETVTITCRASENIYSNLAWYQQKQGKSPQL LVYAATNLADGVPSRFSGSGSGTQYSLKINSLQSEDFGSYYCQ HFWGPPWTFGGGTKLEIKRA |
| 4C1 murine | Heavy chain variable | 33 | QVQLQQSGAELARPGASVKLSCKASGYTFTSYWMQWVKQRP GQGLEWIGTIYPGDGDTRYTQKFKGKATLTADKSSNTAYMQL SSLASEDSAVYYCARFEGRQFAYWGQGTLVTVSA |
| 7D7 (murine) | Light chain variable | 45 | DIVMTQSTAIMSASLGERVTMTCTASSSVSSSYFHWYQQKPGS SPKLWIYSTSNLASGVPARFSGRGSGTSYSLTISSVEAEDAATY YCIIQYIIIISPRTFGGGSKLEIKRA |
| 7D7 (murine) | Heavy chain variable | 41 | QVQLQQSGAFVMKPGASVKISCKATDYIFSRYWIEWVKQRPG HGLEWIGEILPGSGYNNSNDKFKGKATFTADTSSNTAYMQLSS LTFEDSAVYYCARKGTFYTMDIIWGQGISVTVSS |
| 7E11 (murine) | Light chain variable | 53 | DIQMTQSPASLSVSVGETVTITCRASENIYSNLAWYQQKQGKSP QLLVYAATNLADGVPSRFSGSGSGTQYSLKINSLQSEDFGSYYC QHFWGPPWTFGGGTKLEIKRA |
| 7E11 (murine) | Heavy chain variable | 49 | QVQLQQSGAELARPGASVKLSCKASGYTFTSYWMQWIKQRPG QGLEWIGTIYPGDGDTRYTQKFKGKATLTADKSSSTAYMQLSS LASEDSAVYYCARFEGRQFAYWGQGTLVTVSA |
| 10E11 (murine) | Light chain variable | 61 | DIVLTQSPATLSVTPGERVSLSCRASQSVNNYLITWYQQKSIESP RLLISYASQSISGISSRFSGSGSGTDFTLIIIISVETEDFGMYFCQQS NRWPLTFGAGTKLELKRA |
| 10E11 (murine) | Ileavy chain variable | 57 | EVKLEESGGGLVNLGASVKISCKATGYPVSRYWIEWLKQRPGII GPEWIGEILPGSDYANYNEKFKGKATFTADISSNSAYMQLSSLT SEDSAVYYCSRKGAYYALDFWGQGTSVTVSS |
| 3G12 (murine) | Light chain variable | 69 | DIQMTQSPASLSVSVGETVTITCRASENIYSNLAWYQIIKQGKSP QLLVYAATNLADGVPSRFSGGGSGTQYSLKINSLQSEDEGTYY CQHFWGPPWTFGGGTKLEIKRA |
| 3G12 (murine) | Heavy chain variable | 65 | QVQLQQSGAFLARPGASVKLSCKASGYTFTSYWMQWVKQRP GQGLEWIGTIYPGDGDTRYTQKFKGKATLTADKSSSTVYMQLT SLASEDSAVYYCARFYGGAMDSWGQGTSVTVSS |

TABLE 3 -continued

Light Chain and Heavy Chain Variable Region Sequences and Full-length Antibody Sequences of Antibodies

| Name | Region[1] | SEQ ID NO | Sequence |
|---|---|---|---|
| 4B11 (murine) | Light chain variable | 77 | DIVLTQSPASLAVSLGQRATISCRASQSVSTSTYSYVHWYQQKPGQPPKLLIKYASNLESGVPARFSGRGSGTDFTLSIHPVEGEDAATYYCQHISWGNPWTFGGGTKLEIKRA |
| 4B11 (murine) | Heavy chain variable | 73 | EVQLQQSGPELVKPGASVKMSCKASGFTFTDSVLHWVKQKPGQGLEWIGYIHIPYNDDTKFHDSFKGKATLTSDKSSTTAYMELSSLTSEDSAVYYCSRNDELRVALDYWGQGTSVTVSS |
| 5F1 (murine) | Light chain variable | 85 | QIVLTQSPAIMSASPGEKATITCSASSSVSYMIIWFQQRPGTSPKLWTYSTSNLASGVPARFSGSGSGTSFSLTISRMEAEDAATYYCHQRSGHTFTFGSGTKLEIKRA |
| 5F1 (murine) | Heavy chain variable | 81 | DVQLQESGPGLVKPSHSLSLTCTVTGYSITSDYAWNWIRQFPGNNLEWMGYITYSGSTGYNPSLKSRISITRDTSKNQFFLQLNSVTAEDTATYYCARDWPFAYWGQGTLVTVSA |
| 5F6 (murine) | Light chain variable | 93 | DIVLTQSPASLAVSLGQRATISCRASQSVSTSSYSYMHWYQQKPGQPPKLLIKYASNLESGVPARFSGSGSGTDFTLNIHPVEEEDTATYYCQHGWEIPYTFGGGTKLEIKRA |
| 5F6 (murine) | Heavy chain variable | 89 | EVKLEESGGGLVQPGGSLKLSCAASGFTLSRYTMSWVRQTPEKRLEWVAYISNGGGSTYYPDTVKGRFTTSRDNAKNTLYLQMSSLKSEDTAMYYCGRAFAGTDWFAYWGQGTLVTVSA |
| 13G12 (purine) | Light chain variable | 101 | QIVLTQSPAIMSASPGEKVTMTCGASSSVSYMYWFQQKPGSSPRLLIYDTFNLASGVPVRFSGSESGTSYSLTISRMEAEDAATYYCQIIWSSYPPTFGSGTKLEIDRA |
| 13G12 (murine) | Heavy chain variable | 97 | QVQLQQPGTELVKPGASVKLSCKASGYTFTSNWMNWVKQRPGIIGLEWIGNIYPSNGGTNYNEKFKSKATLTVDKSSSTAYMQLRGLTSEDSAVYYCVRTISNYVGAMDYWGQGTSVTVSS |
| 9B3 (murine) | Light chain variable | 109 | DIVMTQSPATLSVTPGERVSLSCRASQSVNNYLHWYQQKSHESPRLLISYVSQSISGISSRFSGSGSGTDFTLIIHSVETEDFGMYFCQQSNRWPLTFGAGTKLELK |
| 9B3 (murine) | Heavy chain variable | 105 | QVQLQQSGAELMNLGASVKISCKATGYPVSRYWIEWLKQRPGHGPEWIGEILPGSDYANYNEKFKGKATFTADISSNSAYMQLSSLTSEDSAVYYCSRKGAYYALDFWGQGTSVTVSS |
| 4F4 (humanized) | Heavy chain variable | 113 | QVQLVQSGAFVKKPGASVKVSCKASGYTFTDHYMNWVRQAPGQGLEWIGDIDPKNGGTLYNQNFKGRATLTVDKSISTAYMELSRLRSDDTAVYYCARREAMDYWGQGTLVTVSS |
| 4E4 (humanized) | Light chain variable | 114 | DVVMTQSPLSLPVTPGEPASISCRSSQSIVYSNGNTYLNWYLQKPGQSPQLLIYKVSNRFSGVPDRFSGSGSGTDFTLKISRVEAEDVGVYYCFQGSHVPWTFGGGTKVEIK |
| 4B11 (humanized) | Heavy chain variable | 115 | EVQLVQSGAEVKKPGASVKVSCKASGFTFTDSVLIIWVRQAPGQRLEWIGYIHPYNDDTKFHDSFKGRATLTSDKSASTAYMELSSLRSEDTAVYYCSRNDELRVALDYWGQGTLVTVSS |
| 4B11 (humanized) | Light chain variable | 116 | EIVLTQSPATLSLSPGERATLSCRASQSVSTSTYSYVHWYQQKPGQAPRLLIKYASNLESGIPARFSGSGSGTDFTLTISSLEPEDFAVYYCQHSWGNPWTFGGGTKVEIK |
| 3F5 (humanized) | Heavy chain variable | 117 | QVQLVQSGAEVKKPGASVKVSCKASGYTFTDHYMHWVRQAPGQGLEWIGDINPNSGGTINNQNFKGRATLTVDKSISTAYMELSRLRSDDTAVYYCARGFSGLAYWGQGTLVTVSS |
| 3F5 (humanized) | Light chain variable | 118 | DIVMTQTPLSSPVTLGQPASISCKSSQSLLDRDGKTYLNWLQQRPGQPPRRLIYLVSILDSGVPDRFSGSGAGTDFTLKISRVEAEDVGVYYCWQGTHFPWTFGQGTKLEIK |
| 10E11 (humanized) | heavy chain variable | 119 | EVQLVQSGAEVKKPGESLRISCKGSGYPVSRYWIEWVRQMPGKGLEWIGEILPGSDYANYNEKFKGIIATFSADISISTAYLQWSSLKASDTAMYYCSRKGAYYALDFWGQGTLVTVSS |
| 10E11 (humanized) | light chain variable | 120 | EIVMTQSPATLSVSPGERATLSCRASQSVNNYLHWYQQKPGQAPRLLISYASQSISGIPARFSGSGSGTEFTLTISSLQSEDFAVYYCQQSNRWPLTFGQGTKLEIK |

TABLE 3 -continued

Light Chain and Heavy Chain Variable Region Sequences and Full-length Antibody Sequences of Antibodies

| Name | Region[1] | SEQ ID NO | Sequence |
|---|---|---|---|
| 4E4 (humanized) | Full heavy chain | 121 | QVQLVQSGAEVKKPGASVKVSCKASGYTFTDHYMNWVRQAP GQGLEWIGDIDPKNGGTLYNQNFKGRATLTVDKSISTAYMELS RLRSDDTAVYYCARREAMDYWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKRV EPKSCDKTIITCPPCPAPELLGGPSVFLFPPKPKDTLMISRTPEVT CVVVDVSHEDPEVKFNWYVDGVEVIINAKTKPREFQYNSTYR VVSVLTVLHQDWLNGKEYKCKVSNKALPAPIEKTISKAKGQPR EPQVYTLPPSRDELTKNQVSLTCLVKGFYPSDIAVEWESNGQPE NNYKTTPPVLDSDGSFFLYSKLTVDKSRWQQGNVFSCSVMIIE ALHNHYTQKSLSLSPGK |
| 4E4 (humanized) | Full light chain | 122 | DVVMTQSPLSLPVTPGEPASISCRSSQSIVYSNGNTYLNWYLQK PGQSPQLLIYKVSNRFSGVPDRFSGSGSGTDFTLKISRVEAEDVG VYYCFQGSIIVPWTFGGGTKVEIKRTVAAPSVFIFPPSDEQLKSG TASVVCLLNNFYPREAKVQWKVDNALQSGNSQESVTEQDSKD STYSLSSTLTLSKADYEKHKVYACEVTHQGLSSPVTKSFNRGEC |
| 4B11 (humanized) | Full heavy chain | 123 | EVQLVQSGAEVKKPGASVKVSCKASGFTFTDSVLIIWVRQAPG QRLEWIGYIHPYNDDTKFHDSFKGRATLTSDKSASTAYMELSS LRSEDTAVYYCSRNDELRVALDYWGQGTLVTVSSASTKQPSVF PLAPSSKSTSGGTAALGCLVKDYFPEPVTVSWNSGALTSGVHT FPAVLQSSGLYSLSSVVTVPSSSLGTQTYICNVNIIKPSNTKVDK RVEPKSCDKTHTCPPCPAPELLGGPSVFLFPPKPKDTLMISRTPE VTCVVVDVSHEDPEVKFNWYVDGVEVHNAKTKPREEQYNST YRVVSVLTVLHIQDWLNGKEYKCKVSNKALPAPIEKTISKAKG QPREPQVYTLPPSRDELTKNQVSLTCLVKGFYPSDIAVEWESNG QPENNYKTTPPVLDSDGSFFLYSKLTVDKSRWQQGNVFSCSVM HEALHNHYTQKSLSLSPGK |
| 4B11 (humanized) | Full light chain | 124 | EIVLTQSPATLSLSPGERATLSCRASQSVSTSTYSYVHWYQQKP GQAPRLLIKYASNLESGIPARFSGSGSGTDFTLTISSLEPEDFAVY YCQHSWGNPWTFGGGTKVEIKRTVAAPSVFIFPPSDEQLKSGT ASVVCLLNNFYPREAKVQWKVDNALQSGNSQESVTEQDSKDS TYSLSSTLTLSKADYEKIIKVYACEVTIIQGLSSPVTKSFNRGEC |
| 3F5 (humanized)-hIgG1 | Full heavy chain | 125 | QVQLVQSGAEVKKPGASVKVSCKASGYTFTDIIYMIIWVRQAP GQGLEWIGDINPNSGGTINNQNFKGRATLTVDKSISTAYMELSR LRSDDTAVYYCARGFSGLAYWGQGTLVTVSSASTKGPSVFPLA PCSRSTSESTAALGCLVKDYFPEPVTVSWNSGALTSGVITFPAV LQSSGLYSLSSVVTVPSSSLGTKTYTCNVDHKPSNTKVDKRVES KYGPPCPPCPAPEFLGGPSVFLFPPKPKDTLMISRTPEVTCVVVD VSQEDPEVQFNWYVDGVEVHNAKTKPREEQFNSTYRVVSVLT VLIQDWLNGKEYKCKVSNKGLPSSIEKTISKAKGQPREPQVYT LPPSQEEMTKNQVSLTCLVKGFYPSDIAVEWESNGQPENNYKT TPPVLDSDGSFFLYSRLTVDKSRWQEGNVFSCSVMHEALHNHY TQKSLSLSLG |
| 3F5 (humanized)-hIgG1 | Full light chain | 126 | DIVMTQTPLSSPVTLGQPASISCKSSQSLLDRDGKTYLNWLQQR PGQPPRRLIYLVSILDSGVPDRFSGSGAGTDFTLKISRVEAEDVG VYYCWQGTIIFPWTFGQGTKLEIKRTVAAPSVFIFPPSDEQLKSG TASVVCLLNNFYPREAKVQWKVDNALQSGNSQESVTEQDSKI) STYSLSSTLTLSKADYEKHKVYACEVTHQGLSSPVTKSFNRGEC |
| 10E11 (humanized)-hIgG1 | Full heavy chain | 127 | EVQLVQSGAFVKKPGESLRISCKGSGYPVSRYWIEWVRQMPG KGLEWIGEILPGSDYANYNEKFKGHATFSADISISTAYLQWSSL KASDTAMYYCSRKGAYYALDFWGQGTLVTVSSASTKGPSVFP LAPSSKSTSGGTAALGCLVKDYFPEPVTVSWNSGALTSGVHITF PAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTY RVVSVLTVLIQDWLNGKEYKCKVSNKALPAPIEKTISKAKGQP REPQVYTLPPSRDELTKNQVSLTCLVKGFYPSDIAVEWESNGQP ENNYKTTPPVLDSDGSFFLYSKLTVDKSRWQQGNVFSCSVMHE ALIINHYTQKSLSLSPGK |
| 10E11VH (G24A/ A67V)-h IgGI [10E11V H(AV)-h IgG1] | Full heavy chain | 128 | EVQLVQSGAEVKKPGESLRISCKASGYPVSRYWIEWVRQMPG KGLEWIGEILPGSDYANYNEKFKGHVTFSADISISTAYLQWSSL KASDTAMYYCSRKGAYYALDFWGQGTLVTVSSASTKGPSVFP LAPSSKSTSGGTAALGCLVKDYFPEPVTVSWNSGALTSGVHITF PAVLQSSGLYSLSSVVTVPSSSLGTQTYICNVNIIKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTY |

TABLE 3 -continued

Light Chain and Heavy Chain Variable Region Sequences and Full-length Antibody Sequences of Antibodies

| Name | Region[1] | SEQ ID NO | Sequence |
|---|---|---|---|
| | | | RVVSVLTVLIQDWLNGKEYKCKVSNKALPAPIEKTISKAKGQP<br>REPQVYTLPPSRDELTKNQVSLTCLVKGFYPSDIAVEWESNGQP<br>ENNYKTTPPVLDSDGSFFLYSKLTVDKSRWQQGNVFSCSVMHE<br>ALHNHYTQKSLSLSPGK |
| 10E11V TT(G24A/ A67V)-h IgGI(3A) [10E11V H(AV)-h IgGI(3A)] | Full heavy chain | 129 | EVQLVQSGAEVKKPGESLRISCKASGYPVSRYWIEWVRQMPG<br>KGLEWIGEILPGSDYANYNEKFKGHVTFSADISISTAYLQWSSL<br>KASDTAMYYCSRKGAYYALDFWGQGTLVTVSSASTKGPSVFP<br>LAPSSKSTSGGTAALGCLVKDYFPEPVTVSWNSGALTSGVHTF<br>PAVLQSSGLYSLSSVVTVPSSSLGTQTYICNVNIIKPSNTKVDKK<br>VEPKSCDKTHTCPPCPAPELLGGPSVFLFPPKPKDTLMISRTPEV<br>TCVVVDVSHEDPEVKFNWYVDGVEVHNAKTKPREEQYNATY<br>RVVSVLTVLHQDWLNGKEYKCKVSNKALPAPLAATISKAKGQP<br>REPQVYTLPPSRDELTKNQVSLTCLVKGFYPSDIAVEWESNGQP<br>ENNYKTTPPVLDSDGSFFLYSKLTVDKSRWQQGNVFSCSVMHE<br>ALHNHYTQKSLSLSPG |
| 10E11V H(G24A/ A67V) hIgG4 [10E11V H(AV)-h IgG4] | Full heavy chain | 130 | FVQLVQSGAFVKKPGESLRISCKASGYPVSRYWIEWVRQMPG<br>KGLEWIGEILPGSDYANYNEKFKGHVTFSADISISTAYLQWSSL<br>KASDTAMYYCSRKGAYYALDFWGQGTLVTVSSASTKGPSVFP<br>LAPCSRSTSESTAALGCLVKDYFPEPVTVSWNSGALTSGVHTFP<br>AVLQSSGLYSLSSVVTVPSSSLGTKTYTCNVDHIKPSNTKVDKR<br>VESKYGPPCPPCPAPEFLGGPSVFLFPPKPKDTLMISRTPEVTCV<br>VVDVSQEDPEVQENWYVDGVEVIINAKTKPREEQFNSTYRVVS<br>VLTVLHQDWLNGKEYKCKVSNKGLPSSIEKTISKAKGQPREPQ<br>VYILPPSQEEMTKNQVSLTCLVKGFYPSDLAVEWESNGQPENN<br>YKTTPPVLDSDGSEFLYSRLTVDKSRWQEGNVFSCSVMIIEALII<br>NHYTQKSLSLSLG |
| humanized | Full light chain | 131 | EIVMTQSPATLSVSPGERATLSCRASQSVNNYLHWYQQKPGQA<br>PRLLISYASQSISGIPARFSGSGSGTEFTLTISSLQSEDFAVYYCQ<br>QSNRWPLTFGQGTKLEIKRTVAAPSVFIFPPSDEQLKSGTASVV<br>CLLNNFYPREAKVQWKVDNALQSGNSQESVTEQDSKDSTYSL<br>SSTLTLSKADYEKHKVYACEVTHQGLSSPVTKSFNRGEC |

Example 1: Production of Anti-GITR Hybridoma Antibodies

Purified human GITR (ECD)-mFc (Kim et al., 2007, Oncol Rep. 18:1189) fusion proteins purchased from Dongda Bioscience were used as antigens, which were fully emulsified with complete Freund's adjuvant (Sigma, Cat No: F5581) of an equal volume, and used to subcutaneously immunize 6-8 week old Balb/c mice (purchased from Zhaoyan (Suzhou) New Drug Research Center Co., Ltd.) at a dose of 50 μg/mouse; and then the same dose of antigens were fully emulsified with incomplete Freund's adjuvant (Sigma, Cat No: F5506) every 2 weeks before being used to subcutaneously immunize the mice three times. After the three times of immunization, serum titers of the mice were measured, and the mice were intraperitoneally booster immunized 3 days before fusion. Using PEG Hybri-Max (Sigma, Cat No: 7181) as a fusion agent, spleen cells of the mice and SP2/0 cells were mixed at a ratio of 4:1. Fused cells were added into a 96-well plate ($1\times10^5$ cells/well), each well containing 0.1 mL of 1X HAT medium (Invitrogen, Cat No: 21060-017). 0.1 mL of HT (Invitrogen, Cat No: 11067-030) medium was added on day 3, the medium was pipetted out of the 96-well plate on day 7, and 0.2 mL of fresh HT medium was added. On day 9, a supernatant was collected for subsequent ELISA and FACS assays.

Example 2: Screening and Analysis of Polyclonal Hybridomas Based on ELISA, FACS, and Reporter Gene Assays These assays were intended to screen and select polyclonal hybridomas that can bind to GITR, block the interaction between GITR-L and GITR, and significantly activate the molecular activity of GITR, and polyclonal hybridomas with a high binding capability and high stimulation activity were selected for subclone to obtain required monoclonal hybridoma antibodies.

After the spleen cells of the immunized mice with high ELISA titers were fused with SP2/0 cells and cultured for 7 days, the hybridoma cells were first subjected to ELISA and FACS assays to determine and select positive hybridomas that could bind to GITR, and then 293T luciferase reporter gene assay was initially conducted to screen and select polyclonal hybridomas having functional responses. In the process, a total of more than forty polyclonal hybridoma antibodies with strong binding to GITR were identified. After the reporter gene assay, polyclonal hybridomas with significant binding and stimulation activities were selected for subsequent subclone screening. The hybridoma cells with strong binding to GITR were cryopreserved in liquid nitrogen.

ELISA assay: a 96-well ELISA plate (Corning®, Cat No: 9018) was inoculated with GITR-ECD-hFc, left standing overnight at 4° C., and washed 3 times with washing buffer (PBS+0.05% Tween® 20), then blocking buffer (PBS+1% BSA (Sigma, Cat No: V90093)) was added, and the 96-well ELISA plate was incubated for 1 hour and washed 3 times; hybridoma supernatant was added, the 96-well ELISA plate was incubated for 1 hour and washed 3 times, 100 μL of goat anti-mouse IgG secondary antibodies (Thermo, Cat No: 31432) diluted at a ratio of 1:10000 was added into each well, and the 96-well ELISA plate was incubated at room temperature for 1 hour and washed 3 times. 100 μL of TMB (Biosubstrate Technologies, Cat No: ES-002) was added into each well and left standing for 3 minutes for color development, then a stop solution (2N $H_2SO_4$) was added at a dose of 100 μL/well to terminate the reaction, and OD450× signal of each sample was measured with a Tecan Spark® microplate reader.

FACS assay for the binding of the antibodies: 50 μL of the hybridoma supernatant tested positive in the foregoing ELISA assay was pipetted and mixed with 50 μL of 293T-GITR cells ($1\times10^5$ cells/well), and the mixture was added into a 96-well plate with a U-shaped bottom and incubated for 1 hour. After the mixture was centrifuged and washed with FACS buffer (PBS+3% FCS) twice, a solution of PE-labeled goat anti-mouse secondary antibodies (BioLegend®, Cat No: 405307) diluted at a ratio of 1:400 was added, the mixture was incubated for 30 minutes, and washed with FACS buffer, and then the PE signals of 293T-GITR cells were detected by using BD C6 flow cytometer.

FACS assay for the blocking effect of the antibodies: FACS assay was conducted by using BD C6 to determine the blocking effect of the hybridoma antibodies on the binding of biotin-labeled human GITR ligands to Jurkat-hGITR cells. Jurkat-hGITR cells were suspended in FACS buffer (PBS containing 3% FBS). Diluted hybridoma antibodies were added into the cell suspension and the mixture was incubated in a 96-well plate for 1 hour at 4° C. Biotin-labeled human GITR ligand proteins were added into the wells of the 96-well plate and incubated for 1 hour at 4° C. After incubation, the 96-well plate was washed 3 times, and mouse anti-biotin PE antibodies (Biolgend, Cat No: 409004) were added and incubated at 4° C. for 0.5 hours. The cells in the 96-well plate were washed 3 times and finally analyzed with BD C6.

Analysis of the function of the hybridoma anti-GITR antibodies in immune activation based on the reporter gene assay of Jurkat-GITR—NF-κB cells: FACS assay of reporter genes was conducted for Jurkat-GITR—NF-κB cell line with anti-GITR hybridoma supernatant. 25000 Jurkat-GITR—NF-κB cells were used in each reaction, these cells were added into each well of the 96-well culture plate, then 50 μL of hybridoma supernatant was further added into each well, and the 96-well culture plate was incubated for 4 hours at 37° C. Cells were lysed with 50 μL of Bright Glo reagent (Promega®, Cat No: E2620), and signals were read under luminescent conditions with Tecan Spark®.

Example 3: Subclone of Polyclonal Hybridoma Cells, Amplification Culture and Antibody Purification of GITR Monoclonal Hybridoma Cells, and DNA Sequence Analysis of Monoclonal Hybridoma Antibodies Subclone is intended to create monoclonal hybridoma cells to obtain monoclonal antibodies. The subclone method is based on a finite dilution procedure to obtain hybridoma cells producing a monoclone in a single well of a 96-well plate. After multiple rounds (3 rounds) of subclone, it was ensured that a resulting monoclone contained no other cellular components. For each round of subclone, ELISA, FACS and reporter gene activation activity assays were conducted. After three rounds of subclone, some of the monoclonal cells with high GITR binding and high stimulation activity were cryopreserved, and the rest were used for cell amplification culture to obtain sufficient monoclonal antibodies for purification and subsequent assays.

A total of 14 types of anti-GITR monoclonal hybridoma cells including 4E1, 8H4, 4E4, 3F5, 4C1, 7D7, 7E11, 10E11, 3G12, 4B11, 5F1, 5F6, 13G12 and 9B3 were cultured and antibody purified. Hybridoma cells were cultured in Dulbecco's Modified Eagle's medium (GIBCO; Invitrogen Corporation, Carlsbad, CA) containing 10% fetal bovine serum, 1% penicillin/streptomycin, 2% L-glutamine, and 1% NaH-COs solution for adjustion. The selected hybridoma cells were then adapted to a serum-free medium and antibodies were purified from the supernatant with Protein-G columns (GE Healthcare). After washing with PBS, bound antibodies were eluted with 0.1 M Glycine (pH 3.0), and then pH neutralized with 2.0 M Tris. Ultra-15 centrifugal concentrator (Amicon) was used for buffer exchange and antibody concentration.

Example 4

Purified 4E1, 8H4, 4E4, 3F5, 4C1, 7D7, 7E11, 10E11, 3G12, 4B11, 5F1, 5F6, 13G12 and 9B3 hybridoma anti-hGITR monoclonal antibodies were further assayed for GITR binding, GITR ligand-blocking effect, GITR activation activity based on the reporter genes, and the property of cross-binding to monkey-derived GITR, and the assays involved ELISA, FACS and reporter gene activation analysis for Jurkat-GITR—NF-κB cells.

ELISA-based and FACS-based assays: the method was similar to the method used in Example 2, except that purified antibodies with determined concentrations were used in the assay, and EC50 and IC50 values were calculated with the antibody concentrations obtained by serial dilution and the corresponding results. Tables 4 to 7 show the assay results of 14 types of antibodies. In addition, the analysis of the property of cross-binding to monkey-derived GITR showed that there were cross-binding reactions between the selected 14 antibodies and monkey-derived GITR.

TABLE 4

ELISA Binding-based EC50 of Hybridoma Anti-GITR Antibodies

| ng/ml | 4E1 | 8H4 | 4E4 | 3F5 | 4C1 | 7D7 | 7E11 | 10E11 | 3G12 | 4B11 | 5F1 | 5F6 | 13G12 | 9B3 |
|---|---|---|---|---|---|---|---|---|---|---|---|---|---|---|
| EC50 | 0.067 | 1.338 | 1.705 | 2.314 | 1.932 | 1.037 | 1.144 | 4.733 | 1.628 | 0.883 | 2.039 | 1.259 | 0.277 | 0.523 |

TABLE 5

| FACS Binding-based EC50 of Hybridoma Anti-GITR Antibodies | | | | | | | | | | | | | | |
|---|---|---|---|---|---|---|---|---|---|---|---|---|---|---|
| ng/ml | 4E1 | 8H4 | 4E4 | 3F5 | 4C1 | 7D7 | 7E11 | 10E11 | 3G12 | 4B11 | 5F1 | 5F6 | 13G12 | 9B3 |
| EC50 | 0.416 | 20.41 | 19.92 | 6.026 | 8.3 | 6.387 | 7.844 | 9.173 | 33.06 | 15.67 | 51.74 | 29.35 | 77.31 | 1.923 |

TABLE 6

| Blocking Effect IC50 of Hybridoma Anti-GITR Antibodies on Binding of GITR-L to GITR Based on FACS Assay | | | | | | | | | | | | | | |
|---|---|---|---|---|---|---|---|---|---|---|---|---|---|---|
| ng/ml | 4E1 | 8H4 | 4E4 | 3F5 | 4C1 | 7D7 | 7E11 | 10E11 | 3G12 | 4B11 | 5F1 | 5F6 | 13G12 | 9B3 |
| EC50 | 12.91 | 457.6 | 112.7 | 906.2 | 97.29 | 102.3 | 70.82 | 89.77 | 322.0 | 318.5 | 1.513 | 118.2 | 4002 | 41.35 |

TABLE 7

| Stimulation Activity of Hybridoma Anti-GITR Antibodies in Jurkat-GITR-NF-κB Cell Reporter Gene Assay | | | | | | | | | | | | | | |
|---|---|---|---|---|---|---|---|---|---|---|---|---|---|---|
| Activity | 4E1 | 8H4 | 4E4 | 3F5 | 4C1 | 7D7 | 7E11 | 10E11 | 3G12 | 4B11 | 5F1 | 5F6 | 13G12 | 9B3 |
| Luc_signal | ++++ | ++ | +++ | +++ | +++ | +++ | +++ | +++ | +++ | +++ | +++ | +++ | ++ | +++ |

The number of + in the table represents the strength of the activity (a greater number of + means stronger activity).

Example 5: Assay of the Activity of Hybridoma GITR Antibodies in Stimulating Jurkat Cells to Release IL-2 Cytokines To determine the immune activation activity of hybridoma anti-GITR antibodies, release of IL2 cytokines from Jurkat-GITR cells was used as one of the evaluation indicators of GITR signaling pathway activation. Jurkat-GITR cells were cultured in RPMI 1640 supplemented with 10% FBS. One day before culture, a 96-well plate was inoculated with goat anti-human IgG (Jackson, Cat No: 109-005-008) and goat anti-mouse IgG (Jackson, Cat No: 115-006-071) and left standing at room temperature overnight. After the wells of the plate were washed, 200 μL of blocking buffer was added, sealed, and incubated at 37° C. for 1 hour. After the plate was washed 3 times with PBS, 40 ng/ml OKT3 (eBioscience@, Cat No: 16-0037-85) was added into the wells and incubated at 37° C. for 1 hour. After the plate was washed again with PBS, 100 μL of Jurkat-GITR cells were added into each well of the 96-well plate ($1\times10^5$ cells per well) with or without diluted GITR antibodies. After incubation at 37° C. for 48 or 72 hours, the 96-well plate was centrifuged and the supernatant was collected to measure IL-2 (R&D Systems, Cat No: DY202). The results are shown in Table 8.

TABLE 8

| Assay of the Activation Activity of Hybridoma Anti-GITR Antibodies on Immune Cells Based on IL-2 Release of Jurkat-GITR Cells | | | | | | | | | | | | | | |
|---|---|---|---|---|---|---|---|---|---|---|---|---|---|---|
| Activity | 4E1 | 8H4 | 4E4 | 3F5 | 4C1 | 7D7 | 7E11 | 10E11 | 3G12 | 4B11 | 5F1 | 5F6 | 13G12 | 9B3 |
| IL2 | ++ | +++ | ++++ | +++ | ++ | +++ | ++ | +++ | ++ | +++ | ++ | ++ | + | +++ |

The number of + in the table represents the strength of the activity (a greater number of + means stronger activity)

Example 6: Assay of Effects of Hybridoma Anti-GITR Antibodies on CD4 T Cell Activation and Cytokine Production To further evaluate the activity of the hybridoma GITR antibodies in activating the GITR signaling pathway, primary lymphocyte effector cells were used in this study to assay the stimulation effects of the antibodies on IL2 and IFNγ cytokine release of immune cells. Human CD4 T cells were purified from human PBMCs using CD4 T cell negative selection purification kit and RPMI 1640 medium supplemented with 10% FBS. One day before the purification of T cells, a 96-well plate was inoculated with goat anti-human IgG (Jackson, Cat No: 109-005-008) and goat anti-mouse IgG (Jackson, Cat No: 115-006-071) and left standing at room temperature overnight. After the wells of the plate were washed, 200 μL of blocking buffer was added, sealed, and incubated at 37° C. for 1 hour. After the plate was washed 3 times with PBS, 40 ng/mL OKT3 (eBioscience®, Cat No: 16-0037-85) was added into the wells and incubated at 37° C. for 1 hour. After the plate was washed with PBS, 100 μL of CD4 T cells were added into each well of the 96-well plate ($1\times10^5$ cells per well) with or without diluted GITR antibodies. After incubation at 37° C. for 48 or 72 hours, the 96-well plate was centrifuged, the supernatant was collected, and then ELISA kit (R&D Systems) was used to measure IL-2 (R&D Systems, Cat No: DY202) and IFN-γ (Cat No: DY285). The results are shown in Table 9.

TABLE 9

Activation Activity of Hybridoma Anti-GITR Antibodies on Immune Cells Based on the Assay of IL-2 and IFNg Release of Primary CD4 T Cells.

| Activity | 4E1 | 8H4 | 4E4 | 3F5 | 4C1 | 7D7 | 7E11 | 10E11 | 3G12 | 4B11 | 5F1 | 5F6 | 13G12 | 9B3 |
|---|---|---|---|---|---|---|---|---|---|---|---|---|---|---|
| IL2 | +++ | NA | +++ | NA | ++ | ++++ | ++ | +++ | ++ | ++++ | ++ | ++ | NA | ++++ |
| IFN-g | +++ | NA | ++++ | NA | +++/− | +++++ | +++ | +++ | +++ | ++++ | +++ | ++++/− | NA | +++ |

The number of + in the table represents the strength of the activity (a greater number of + means stronger activity)

Example 7: CDNA Clone and Sequence Analysis of GITR Hybridoma Monoclonal Antibodies DNA sequencing was performed to the 14 anti-GITR monoclonal hybridoma antibodies 4E1, 8H4, 4E4, 3F5, 4C1, 7D7, 7E11, 10E11, 3G12, 4B11, 5F1, 5F6, 13G12 and 9B3. The corresponding amino acid sequence analysis results are shown in Tables 1 to 3.

The clonal analysis of the GITR antibody variable region genes included the following steps: the GITR monoclonal hybridoma cells were lysed with TRIzol™ (Cwbiotech, Cat No: CW0580), and the total RNA of the hybridoma cells was extracted. The RNA of the hybridoma cells was reversely transcribed into cDNA by using HiFi Script™ cDNA Synthesis Kit (Cwbiotech, Cat No: CW2569). The heavy chain and light chain variable region genes of the antibodies were amplified in a PCR method using the cDNA as a template, and degenerate primers (Kettleborough et al. (1993) Eur. J Immunology 23:206-211; Strebe et al. (2010) Antibody Engineering 1:3-14). Reactions were performed in a S1000™ thermal cycler (Bio-Rad, CAT No: 184-2000) for 30 cycles: denaturation at 94° C. for 1.5 minutes; annealing at 50° C. for 1 minute; and synthesis at 72° C. for 1 minute. At the end of the 30th cycle, the reacting mixture was incubated at 72° C. for 7 more minutes for extension.

Electrophoresis of the POR mixture was run on a 1% agarose/Tris-borate gel containing 0.5 μg/mL ethidium bromide. DNA fragments of an expected size (approximately 400 bp for heavy and light chains) were excised from the gel and purified. 3 μL of the purified PCR product was cloned into a pMD-18T vector (Takara, CAT No: D101A), to transform DH5a competent cells, and the DH5a competent cells were inoculated and cultured overnight at 37° C. Monoclones were picked from the culture plate and cultured for amplification, then plasmids were extracted, and the gene sequences of the antibodies were identified. Based on the gene sequences of the antibodies, the complementarity-determining regions (CDRs) and framework regions of the antibodies were analyzed.

The amino acid sequences of the CDR regions of the heavy chains and the light chains of the antibodies are shown in Table 1 and Table 2. The full-length amino acid sequences of the variable regions of the heavy chains and the light chains of the antibodies are shown in Table 3. The variable region sequences (see the table) of 14 antibodies 4E1, 8H4, 4E4, 3F5, 401, 7D7, 7E11, 10E11, 3G12, 4B11, 5F1, 5F6, 13G12 and 9B3 including respective light-chain variable sequences with SEQ ID NOs: 5, 13, 21, 29, 37, 45, 53, 61, 69, 77, 85, 93, 101 and 109, and respective heavy-chain variable sequences with SEQ ID NOs: 1, 9, 17, 25, 33, 41, 49, 57, 65, 73, 81, 89, 97 and 105, were amplified through respective hybridoma cloning. These antibodies showed some required functions, for example, GITR stimulation, increased T cell activation and cytokine release.

Example 8: Humanization of GITR Monoclonal Hybridoma Antibodies

After comprehensive analysis and comparison (including those of the GITR-binding capacity, GITR ligand-blocking effect, GITR and immune cell activation activity, DNA sequencing of the antibodies, and the like) of the 14 anti-GITR monoclonal hybridoma antibodies 4E1, 8H4, 4E4, 3F5, 4C1, 7D7, 7E11, 10E11, 3G12, 4B11, 5F1, 5F6, 13G12 and 9B3, 4 anti-GITR monoclonal hybridoma antibodies 10E11, 4E4, 4B11 and 3F5 were selected for subsequent humanization transformation of GITR antibodies.

GITR antibodies were humanized in a complementarity-determining region grafting method. Firstly, the human germline antibody sequences with the maximum homology to the light chain and heavy chain variable regions of the murine-derived antibodies 10E11, 4E4, 4B11 and 3F5 were searched in the IMGT database. For the antibody 10E11, germline IGKV3-15*01 was selected for the humanization of the light chain variable region, and IGHV5-10-1*01 was selected for the humanization of the heavy chain variable region. For the antibody 4E4, germline IGKV2-28*01 was selected for the humanization of the light chain variable region, and IGHV1-2*06 was selected for the humanization of the heavy chain variable region. For the antibody 4B11, IGKV3-11*01 was selected for the humanization of the light chain, and IGHV1-3*01 was selected for the humanization of the heavy chain. For the antibody 3F5, IGKV2-24*01 was selected for the humanization of the light chain, and IGHV1-2*02 was selected for the humanization of the heavy chain. The CDR regions of the murine-derived antibodies were retained, and the framework sequences of the murine-derived antibodies were replaced with the framework sequences of the human germline antibodies. Secondly, structural models of the murine-derived antibodies were established, and different amino acid sites between the structural models of the human antibodies and those of the corresponding murine-derived antibodies were compared one by one. If the spatial structure of the CDR region was not damaged or changed when a human amino acid sequence was used at a specific site in the framework, the human amino acid sequence would be used at the specific site, otherwise, the corresponding murine-derived sequence would be used at the site (that is, reverse mutation to the murine-derived sequence). Based on the structure simulation, some amino acids of the framework regions of the humanized antibodies 10E11, 4E4, 4B11 and 3F5 were reversely mutated to the murine-derived sequences.

Therefore, the CDR amino acid sequences of the human antibodies in the above template were replaced with the CDR amino acid sequences of the mouse antibodies 4E4, 10E11, 4B11 and 3F5, respectively. In addition, the essential amino acid sequences of the VHs and VLs of the mouse antibodies 4E4, 10E11, 4B11 and 3F5 were grafted into the frameworks of the VHs and VLs of the human antibodies in the above template, respectively, to obtain functionally humanized antibodies. In addition, for the VHs and VLs of 4E4, 10E11, 4B11 and 3F5, several sites of the framework amino acids of the human antibodies in the above template were reversely mutated to the corresponding amino acid sequences of the mouse antibodies 4E4, 10E11, 4B11 and 3F5.

For the humanized heavy chain of the antibody 10E11, Gly at the $24^{th}$ site was reversely mutated to Ala, Ser at the $28^{th}$ site was reversely mutated to Pro, Phe at the $29^{th}$ site was reversely mutated to Val, Thr at the $30^{th}$ site was reversely mutated to Ser, Met at the $48^{th}$ site was reversely mutated to Ile, Ile at the $69^{th}$ site was reversely mutated to Phe, Lys at the $73^{rd}$ site was reversely mutated to Ile, and Ala at the $93^{rd}$ site was reversely mutated to Ser. For the humanized light chain of the antibody 10E11, Tyr at the $49^{th}$ site was reversely mutated to Ser. For the humanized heavy chain of the antibody 4E4, Met at the $48^{th}$ site was reversely mutated to Ile, Val at the $67^{th}$ site was reversely mutated to Ala, Met at the $69^{th}$ site was reversely mutated to Leu, Arg at the $71^{th}$ site was reversely mutated to Val, and Thr at the $73^{th}$ site was reversely mutated to Lys. For the humanized light chain of the antibody 4E4, Ile at the second site was reversely mutated to Val. For the humanized heavy chain of the antibody 4B11, Tyr at the $27^{th}$ site was reversely mutated to Phe, Met at the $48^{th}$ site was reversely mutated to Ile, Val at the $67^{th}$ site was reversely mutated to Ala, Ile at the $69^{th}$ site was reversely mutated to Leu, Arg at the $71^{rd}$ site was reversely mutated to Ser, and Thr at the $73^{rd}$ site was reversely mutated to Lys. For the humanized light chain of the antibody 4B11, Tyr at the $49^{th}$ site was reversely mutated to Lys. Met at the $48^{th}$ site of a humanized heavy chain of the antibody 3F5 was reversely mutated to Ile, Val at the $67^{th}$ site was reversely mutated to Ala, Met at the $69^{th}$ site was reversely mutated to Leu, Arg at the $71^{th}$ site was reversely mutated to Val, and Thr at the $73^{th}$ site was reversely mutated to Lys. For the humanized light chain of the antibody 3F5, Leu at the $46^{th}$ site was reversely mutated to Arg.

The amino acid sequence numbers of the heavy chain and light chain variable regions of the humanized antibody 10E11 are SEQ ID NO: 119 and SEQ ID NO: 129, respectively. The amino acid sequence numbers of the heavy chain and light chain variable regions of the humanized antibody 4E4 are SEQ ID NO: 113 and SEQ ID NO: 114, respectively. The amino acid sequence numbers of the heavy chain and light chain variable regions of the humanized antibody 4B11 are SEQ ID NO: 115 and SEQ ID NO: 116, respectively. The amino acid sequence numbers of the heavy chain and light chain variable regions of the humanized antibody 3F5 are SEQ ID NO: 117 and SEQ ID NO: 118, respectively. The IgG1 subtypes of the humanized antibodies 10E11, 4E4, 4B11, and 3F5 were constructed; and human IgG1 (hIgG1) versions of the humanized antibodies 4E4, 10E11, and 4B11, a hIgG1 (3A) version of the humanized antibody 10E11, and hIgG4 versions of the humanized antibodies 10E11 and 3F5: h10E11-hIgG1, h4E4-hIgG1, h4B11-hIgG1, h10E11-hIgG1 (3A), h10E11-hIgG4, and h3F5-hIgG4, were produced. As shown in Table 3, the amino acid sequences include h4E4-IgG1 [SEQ ID NOs: 121 (full-length heavy chain) and 122 (full-length light chain)], h10E11-IgG1 [(SEQ ID NOs: 127 and 128 (full-length heavy chain) and 131 (full-length light chain)]; h10E11-IgG1 (3A) [(SEQ ID NOs: 129 (full-length heavy chain) and 131 (full-length light chain))], h10E11-IgG4 [(SEQ ID NOs: 130 (full-length heavy chain) and 131 (full-length light chain))], h4B11-IgG1 [(SEQ ID NOs: 123 (full-length heavy chain) and 124 (full-length light chain))] and h3F5-IgG1 [(SEQ ID NOs: 125 (full-length heavy chain) and 126 (full-length light chain))].

Construction and expression of the humanized antibodies 4E4, 10E11, 4B11, and 3F5: the DNA encoding the light and heavy chains of the humanized antibodies was synthesized and cloned into expression vector pcDNA3.1 (Invitrogen, CAT No: #V-790). FreeStyle™ 293 cells (200 mL, 106/mL) were transfected with 100 μg of each type of the humanized heavy and light chain expression plasmid and cultured for 6 days. Then, the humanized antibodies were purified from the supernatant with Protein-G columns (GE Healthcare).

Example 9

The binding of the humanized antibodies to GITR was determined via ELISA and FACS, the GITR ligand-blocking activity was determined via FACS, and the immune activation response of the humanized antibodies was analyzed based on the Jurkat-GITR—NF-κB cell reporter gene assay.

After production and purification of the humanized antibodies, the binding and specificity of the antibodies were determined via ELISA and FACS-based binding assays and assay of the blocking of the binding of Jurkat-GITR cells to GITR-L. The method used was similar to the methods described in Examples 2 and 4.

In the ELISA-based binding assay, it was shown that the humanized antibodies significantly bound to GITR, as shown in FIG. 1, the EC50 for the binding of the humanized anti-GITR antibodies to GITR-mFc protein was detected via ELISA; and the humanized anti-GITR antibodies included h10E11 (AV)-hIgG1 (3A), h10E11 (AV)-hIgG4, h4E4-hIgG1, h4B11-hIgG1 and h3F5-hIgG1. An upper part of the figure shows the absorbance values of the humanized antibodies or the control hIgG1 having a series of concentrations. As indicated by the X axis, the concentrations of the test antibodies were 20000 ng/ml, 2000 ng/ml, 200 ng/mL, 20 ng/ml, 2 ng/ml, 0.2 ng/mL, 0.02 ng/mL, 0.002 ng/ml, 0.0002 ng/mL, and 0.00002 ng/ml. The table at the bottom of the figure shows the calculated EC50 for each type of the test antibodies. As shown in the figure, all the humanized antibodies significantly bound to GITR-mFc inoculated in plates, and h4B11-hIgG1 and h10E11 (AV)-hIgG1 (3A) had stronger binding.

Figure 2:
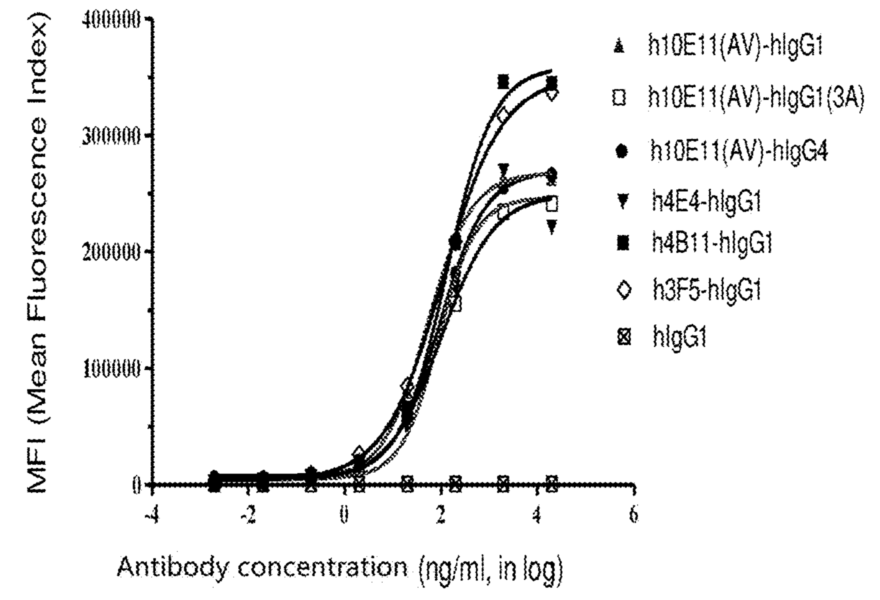
FIG. 2 shows the result of the binding of the humanized GITR antibodies to GITR on a cell membrane in FACS assay.

FIG. 2 shows the binding to GITR on Jurkat-GITR cells based on FACS. The bottom table provides the EC50 of each type of the humanized antibodies. 4B11-hIgG1 and 10E11 (AV)-hIgG1 were the main conjugates based on FACS assay. The humanized GITR antibodies included h10E11 (AV)-hIgG1, h10E11 (AV)-hIgG1 (3A), h10E11 (AV)-hIgG4, h4E4-hIgG1, h4B11-hIgG1, h3F5-hIgG1 and a negative control (human IgG1). An upper part of the figure shows the mean fluorescence indexes of the humanized antibodies or the control hIgG1 having a series of concentrations. The bottom part shows the calculated EC50 of each type of the test antibodies. The results showed that all the humanized antibodies significantly bound to Jurkat-GITR cells. In addition, the humanized antibodies h4E4 and h10E11 (AV) were the main binders. As indicated by the X axis, the concentrations of the test antibodies were 20000 ng/ml, 2000 ng/ml, 200 ng/ml, 20 ng/ml, 2 ng/ml, 0.2 ng/ml, 0.02 ng/ml, and 0.002 ng/ml, respectively.

Figure 3:
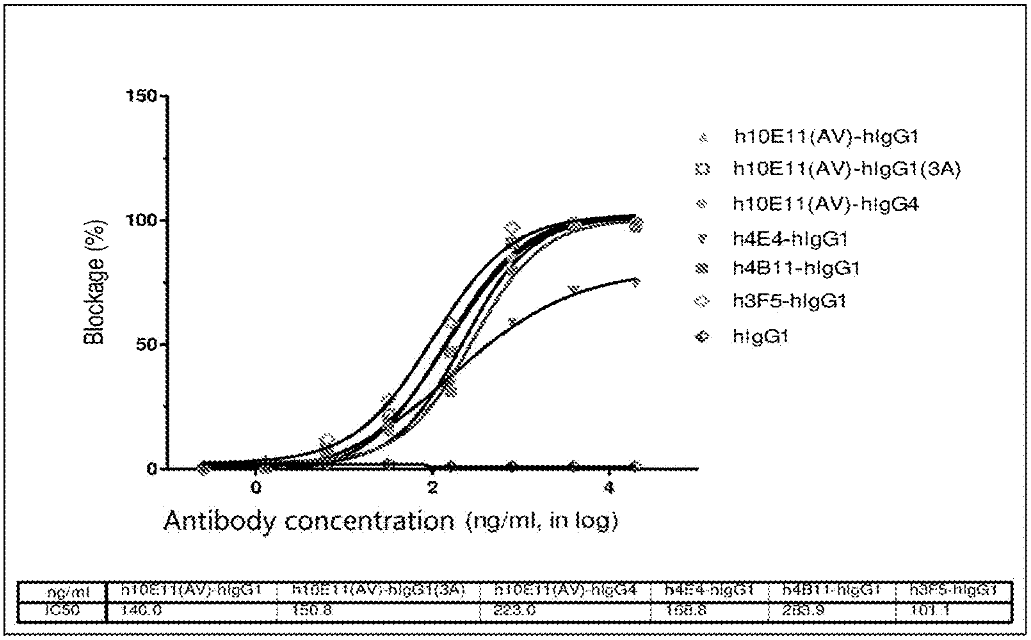
FIG. 3 shows the blocking effect of the humanized GITR antibodies on the binding of GITR-L to Jurkat-GITR cells.

FIG. 3 shows the blocking of the binding of GITR-L to GITR by the humanized antibodies on Jurkat-GITR cells.

The concentration of the GITR-L used was 0.25 μg/mL. The test GITR antibodies included h10E11 (AV)-hIgG1, h10E11 (AV)-hIgG1 (3A), h10E11 (AV)-hIgG4, h4E4-hIgG1, h4B11-hIgG1, h3F5-hIgG1 and a negative control (human IgG1). As indicated by the X axis, the concentrations of the test antibodies were 20000 ng/ml, 4000 ng/mL, 800 ng/mL, 160 ng/ml, 32 ng/ml, 6.4 ng/ml, 1.28 ng/ml, and 0.256 ng/ml, respectively. The results showed that all of the humanized GITR antibodies showed certain blocking activity on the binding of GITR-L to Jurkat-GITR cells. The humanized antibodies h10E11 (AV) and h3F5 had better blocking effects.

Figure 4:
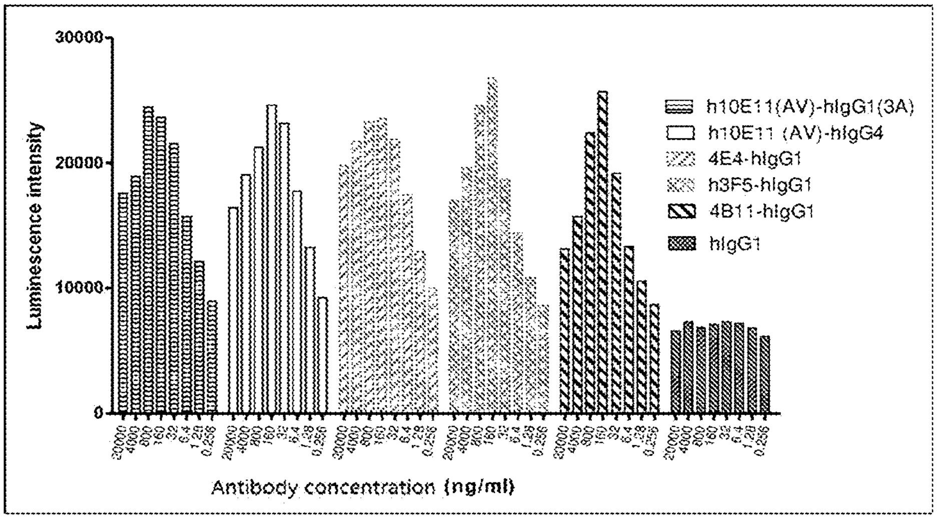
FIG. 4 shows the GITR activation activity of the humanized anti-GITR antibodies via 293T-GITR-NFkb-luc cell reporter gene assay.

FIG. 4 shows the GITR activation activity of the humanized anti-GITR antibodies via 293T-GITR-NFkb-luc cell reporter gene assay. The test anti-GITR antibodies included h10E11 (AV)-hIgG1 (3A), h10E11 (AV)-hIgG1, h4E4-hIgG1, h4B11-hIgG1, h3F5-hIgG1 and a negative control (human IgG1). The concentrations of the test antibodies were 20000 ng/ml, 4000 ng/ml, 800 ng/ml, 160 ng/ml, 32 ng/ml, 6.4 ng/ml, 1.28 ng/ml, and 0.256 ng/ml, respectively. The results showed that all of the humanized antibodies had strong activation activity for the expression of the luciferase reporter gene in 293T-GITR-NFkb-luc cells. Similar activity was observed among the test humanized antibodies.

Example 10: Activation Test of the Humanized Anti-GITR Antibodies via Jurkat-GITR IL-2 Release Assay To test the activation activity of the hybridoma anti-GITR antibodies, the antibodies were first evaluated by their stimulation effects on GITR signaling pathway in Jurkat-GITR cells. Jurkat-GITR, 293T-OKT3, 293T-CD32A and 293T cells were each cultured in RPMI 1640 supplemented with 10% FBS. 50 μL of Jurkat-GITR ($1\times10^5$ cells per well), 50 μL of 293T-OKT3 ($2\times10^4$ cells per well), and 50 μL of 293T-CD32A or 293T ($2\times10^4$ cells per well) cells were added into individual wells of a 96-well plate. It was determined whether there were diluted GITR antibodies. After incubation at 37° C. for 48 or 72 hours, the 96-well plate was centrifuged and the supernatant was collected to measure IL-2 (R&D Systems, Cat No: DY202).

Figure 5:
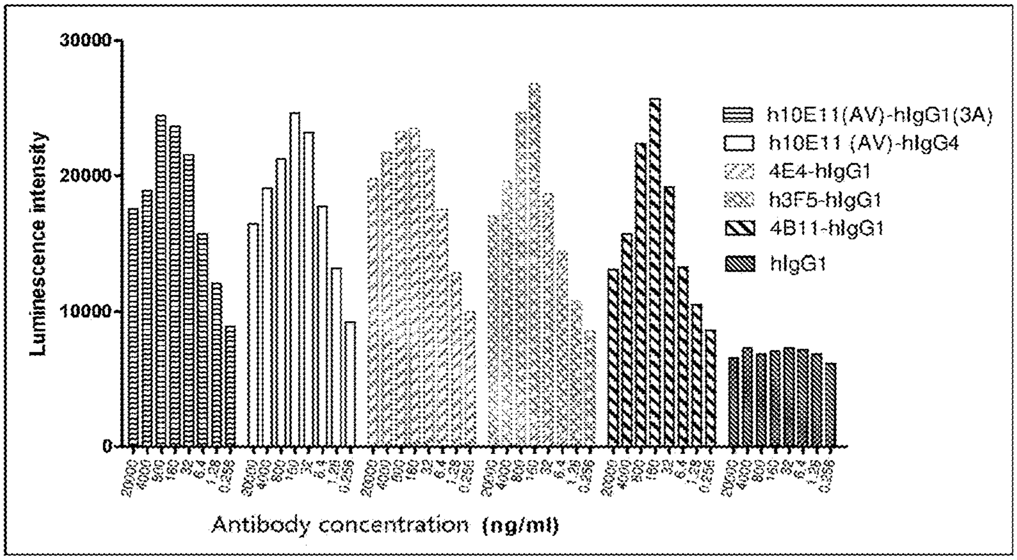
FIG. 5 shows the result of the activation of Jurkat-GITR cells by the humanized GITR antibodies to release cytokine IL2 without cross-linking.

FIG. 5 shows the result of the activation of Jurkat-GITR cells by the humanized GITR antibodies to release cytokine IL2 without cross-linking. Jurkat-GITR cells were stimulated by OKT3 in 293T-OKT3 cells to some extent. The test anti-GITR antibodies included h10E11 (AV)-hIgG1 (3A), h10E11 (AV)-hIgG1, h4E4-hIgG1, h4B11-hIgG1, h3F5-hIgG1 and a negative control (human IgG1). The concentrations of the test antibodies were 20000 ng/ml, 4000 ng/ml, 800 ng/ml, 160 ng/ml, 32 ng/ml, 6.4 ng/mL, 1.28 ng/ml, and 0.256 ng/mL, respectively, As shown in the figure, all the humanized antibodies can stimulate, to some extent, Jurkat-GITR cells to release IL2 without cross-linking.

Figure 6:
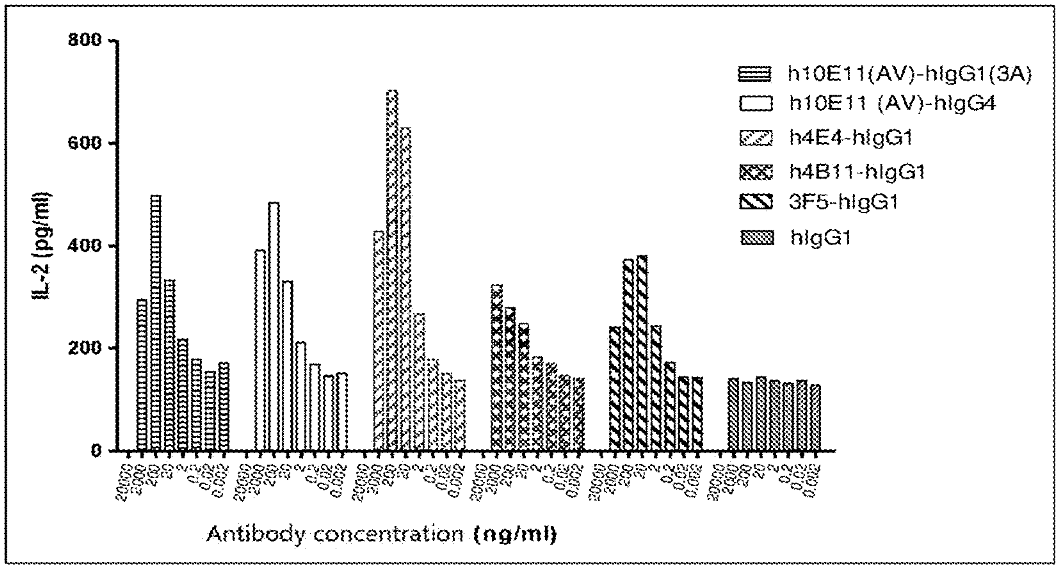
FIG. 6 shows the result of the activation of Jurkat-GITR cells by the humanized GITR antibodies to release cytokine IL2 with cross-linking.

FIG. 6 shows the result of the activation of Jurkat-GITR cells by the humanized GITR antibodies to release cytokine IL2 with cross-linking. The cross-linking factor is CD32a expressed in 293T-CD32a cells. Jurkat-GITR cells were stimulated by OKT3 in 293T-OKT3 cells to some extent. The test anti-GITR antibodies included h10E11 (AV)-hIgG1 (3A), h10E11 (AV)-hIgG1, h4E4-hIgG1, h4B11-hIgG1, h3F5-hIgG1 and a negative control (human IgG1). The concentrations of the test antibodies were 20000 ng/mL, 4000 ng/ml, 800 ng/ml, 160 ng/ml, 32 ng/ml, 6.4 ng/ml, 1.28 ng/ml, and 0.256 ng/ml, respectively. As shown in the figure, all the humanized antibodies exhibited stronger stimulation activity on IL2 release from Jurkat-GITR cells (especially h4E4-hIgG1) with cross-linking.

Example 11: Effect of Humanized Anti-GITR Antibodies on Cytokine Production by CD4+ T Cells The activity of the GITR hybridoma antibodies was evaluated by their stimulation effect on GITR signaling pathway in lymphocyte effector cells. Human CD4+ T cells were purified from PBMCs by using CD4+ negative selection kit in RPMI 1640 supplemented with 10% FBS. One day before culture, a 96-well plate was inoculated with goat anti-human IgG (Jackson, Cat No: 109-005-008) and goat anti-mouse IgG (Jackson, Cat No: 115-006-071) and left standing at room temperature overnight. After the wells were washed, 200 μL of blocking buffer was added, sealed, and incubated at 37° C. for 1 hour. After the plate was washed 3 times with PBS, 40 ng/ml OKT3 (eBioscience®, Cat No: 16-0037-85) was added into the wells and incubated at 37° C. for 1 hour. After the plate was washed with PBS, 100 L of CD4+ T cells were added into each well of the 96-well plate ($1\times10^5$ cells per well) with or without diluted GITR antibodies. After incubation at 37° C. for 48 or 72 hours, the 96-well plate was centrifuged, the supernatant was collected, and ELISA kit (R&D Systems) was used to measure IL-2 (R&D Systems, Cat No: DY202) and IFN-γ (Cat No: DY285).

Figure 7:
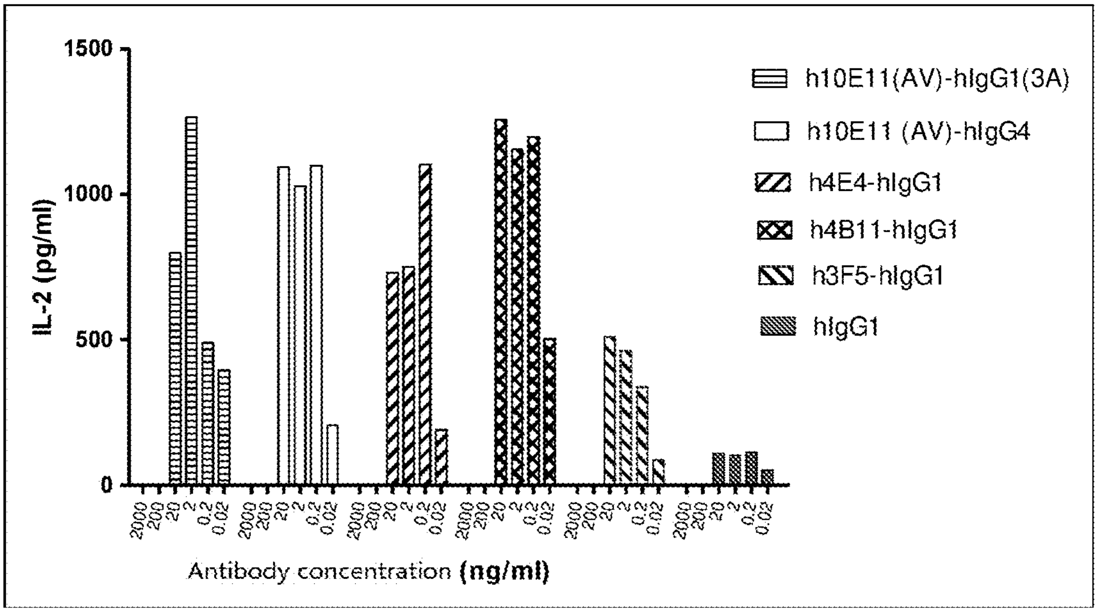
FIG. 7 shows the effect of the humanized GITR antibodies on the production of cytokine IL2 by CD4 T cells.

FIG. 7 shows the effect of the humanized GITR antibodies on the production of cytokine IL2 by CD4+ T cells. The test anti-GITR antibodies included h10E11 (AV)-hIgG1 (3A), h10E11 (AV)-hIgG1, h4E4-hIgG1, h4B11-hIgG1, h3F5-hIgG1 and a negative control (human IgG1). The concentrations of the test antibodies were 20 ng/ml, 2 ng/mL, 0.2 ng/ml, and 0.02 ng/ml, respectively. As shown in the figure, the humanized antibodies 10E11, 4B11 and 4E4 (in particular, h4B11-hIgG1) had significant stimulation effects on the cytokine IL2 production by the primary CD4 T cells; and the humanized 3F5 antibody in this assay showed relatively low activity.

Figure 8:
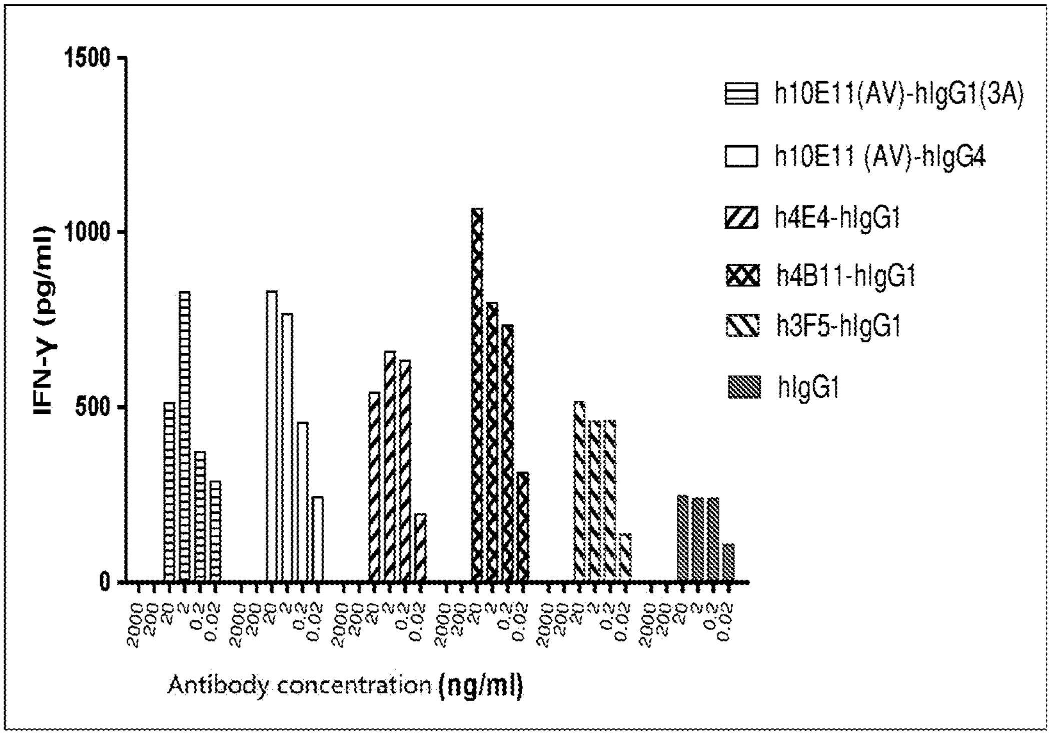
FIG. 8 shows the effect of the humanized GITR antibodies on the production of cytokine IFN-γ by CD4 T cells.

FIG. 8 shows the effect of the humanized GITR antibodies on the production of cytokine IFN-γ by CD4+ T cells. The test anti-GITR antibodies included h10E11 (AV)-hIgG1 (3A), h10E11 (AV)-hIgG1, h4E4-hIgG1, h4B11-hIgG1, h3F5-hIgG1 and a negative control (human IgG1). The concentrations of the antibodies were 20 ng/ml, 2 ng/ml, 0.2 ng/ml, and 0.02 ng/ml, respectively. As shown in the figure, the humanized antibodies 10E11, 4B11 and 4E4 (in particular, h4B11-hIgG1) had significant stimulation effects on the cytokine IFN-γ production of the primary CD4 T cells; and the humanized 3F5 antibody in this assay showed relatively low activity. The results indicated a similar pattern to that of IL2 production in FIG. 7. That is, the humanized antibodies 10E11, 4B11 and 4E4 had significant stimulation effects on the IL2 production of the primary CD4 T cells. The humanized 3F5 antibody showed relatively low activation activity.

Example 12: Biacore™ Kinetics Test of Humanized Anti-GITR Antibodies 4E4, 10E11, 4B11 and 3F5

To characterize the binding properties of the humanized antibodies, the binding kinetics between GITR and anti-GITR antibodies was measured with Biacore™ 3000 and recorded at a data collection rate of 1 Hz. Polyclonal rabbit anti-mouse IgG (GE, BR-1008-38) was diluted with 10 mM sodium acetate (pH 5.0) and immobilized in reference and test flow cells of a CM5 biosensor chip to about 15000RU by using an amine coupling kit (GE, BR10050). At the beginning of each cycle, diluted test antibodies (1.5 μg/mL) were injected into the test flow cell for 1 minute to be captured. Preparation method of GITR analyte series included: a stock solution was diluted to have a concentration of 100 nM with a running buffer, followed by 2-fold serial dilutions to have a concentration of 0.78 nM with the same buffer. The analytes were continuously injected into the reference and test flow cells at a flow rate of 30 L/min for 3 minutes. Then, a running buffer (PBS containing 0.05% P20) was injected at a flow rate of 30 μL/min for 10 minutes. At the end of each cycle, 10 mM glycine-HCl buffer (pH 1.7) was injected at a flow rate of 10 μL/min for 3 minutes for regeneration on the biosensor surface. For each injection of the analyte sample (that is, each cycle), dual reference was performed to the binding responses obtained on a test biosensor surface by subtracting simultaneously recorded responses from a reference surface and subtracting responses from a single reference running buffer sample. Association and dissociation rate constants (ka and kd) may be both determined by fitting dual-reference sensorgrams of the entire titration series to Langmuir model (1:1) with Biaevaluation 4.0 software. A dissociation constant KD is calculated by using the determined rate constant via a formula KD=kd/ka. As shown in Table 10, the humanized anti-GITR antibodies bound to human GITR with high affinity, especially humanized 4B11 and 10E11.

TABLE 10

GITR-his multi-cycle kinetics test by SPR

| Antibody | Ka (1/MS) | Kd (1/S) | KD (M) |
|---|---|---|---|
| Humanized 10E11 | 4.24E+05 | 2.93E−04 | 6.91E−10 |
| Humanized 4E4 | 3.25E+05 | 1.23E−03 | 3.78E−09 |
| Humanized 4B11 | 1.73E+06 | 2.57E−04 | 1.49E−10 |

Biacore ™ T200 test; Model: kinetics, 1:1 binding; KD = kd/ka

The results of the foregoing examples show that the monoclonal antibody or the antigen-binding fragment thereof according to the present disclosure, or the monoclonal antibody conjugate comprising the monoclonal antibody or the antigen-binding fragment thereof according to the present disclosure has good application potential in preparation of medications for activating GITR signaling, medications for activating T lymphocytes, medications for increasing the expression of IL-2 and INF-γ in T lymphocytes, medications for blocking the binding of GITR-L to GITR, and medications for preventing, treating, and/or assistantly treating tumors.

The foregoing embodiments are only preferable embodiments of the present disclosure. It should be noted that a person of ordinary skills in the art could also make changes without departing from the principle of the present disclosure. These changes shall also be construed as falling within the protection scope of the present disclosure.

What is claimed is:

1. An anti-GITR monoclonal antibody or an antigen-binding fragment thereof, which comprises a heavy chain variable region (VH) and a light chain variable region (VL), wherein the VH comprises a VH complementarity determining region 1 (VH CDR1), VH CDR 2 and VH CDR 3 and the VL comprises a VL CDR1, VL CDR 2 and VL CDR 3, wherein the VH CDR1, VH CDR2, VH CDR3, VL CDR1, VL CDR2 and VL CDR3 comprises the amino acid sequence of SEQ ID NO: 74, 75, 76, 78, 79 and 80, respectively.

2. The anti-GITR monoclonal antibody or the antigen-binding fragment thereof according to claim 1, wherein the VH comprises the amino acid sequence of SEQ ID NO: 73 and the VL comprises the amino acid sequence of SEQ ID NO:77.

3. The anti-GITR monoclonal antibody or the antigen-binding fragment thereof according to claim 1, wherein the VH and the VL are humanized and comprise the amino acid sequence of SEQ ID NO: 115 and 116, respectively.

4. The anti-GITR monoclonal antibody or the antigen-binding fragment thereof according to claim 3, comprising a heavy chain and a light chain comprising the amino acid sequence of SEQ ID NO: 123 and 124, respectively.

5. A method of blocking binding of GITR-L to GITR, activating T lymphocytes, or increasing expression of IL-2 and/or IFN-γ in T lymphocytes comprising contacting T lymphocytes with an effective amount of the anti-GITR monoclonal antibody or the antigen-binding fragment thereof according to claim 1.

6. A monoclonal antibody conjugate, comprising a monoclonal antibody and a conjugating part, wherein the monoclonal antibody is the anti-GITR monoclonal antibody or the antigen-binding fragment thereof according to claim 1, and the conjugating part is selected from one or more of the group consisting of a radionuclide, a medication, a toxin, a cytokine, a cytokine receptor fragment, an enzyme, fluorescein, and biotin.

7. A method of blocking binding of GITR-L to GITR, activating T lymphocytes, or increasing expression of IL-2 and/or IFN-γ in T lymphocytes comprising contacting the T lymphocytes with an effective amount of the monoclonal antibody conjugate according to claim 6.

8. A polynucleotide comprising a nucleotide sequence encoding the anti-GITR monoclonal antibody or the antigen-binding fragment thereof according to claim 1.

* * * * *

SEQUENCE LISTING

```
<160> NUMBER OF SEQ ID NOS: 131

<210> SEQ ID NO 1
<211> LENGTH: 118
<212> TYPE: PRT
<213> ORGANISM: Mus musculus

<400> SEQUENCE: 1

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Arg Asn Ser Gly Thr Thr Ser Tyr Asn Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Thr Arg Ser Gly His His Asp Leu Phe Asp Tyr Trp Gly Gln Gly Thr
            100                 105                 110

Thr Leu Thr Val Ser Ser
        115


<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2
```

Ser Asp Tyr Ala Trp Asn
1               5

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Tyr Ile Arg Asn Ser Gly Thr Thr Ser Tyr Asn Pro Ser Leu Lys Ser
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Ser Gly His His Asp Leu Phe Asp Tyr
1               5

<210> SEQ ID NO 5
<211> LENGTH: 114
<212> TYPE: PRT
<213> ORGANISM: Mus musculus

<400> SEQUENCE: 5

Asp Val Val Met Thr Gln Thr Pro Leu Thr Leu Ser Phe Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Gln Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Ala

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Lys Ser Ser Gln Ser Leu Leu Asp Ser Asp Gly Lys Thr Tyr Leu Asn
1               5                   10                  15

<210> SEQ ID NO 7
<211> LENGTH: 7
<212> TYPE: PRT
<213> ORGANISM: Artificial Sequence

```
<220> FEATURE:
<223> OTHER INFORMATION: Synthetic peptide

<400> SEQUENCE: 7

Leu Val Ser Glu Leu Asp Ser
1               5


<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Trp Gln Gly Thr His Phe Pro Trp Thr
1               5


<210> SEQ ID NO 9
<211> LENGTH: 116
<212> TYPE: PRT
<213> ORGANISM: Mus musculus

<400> SEQUENCE: 9

Glu Val Gln Leu Gln Gln Ser Gly Pro Glu Leu Val Arg Pro Gly Ala
1               5                   10                  15

Ser Val Asn Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asn Ile Asn Pro Asn His Asp Tyr Thr Ser Tyr Asn Gln Lys Phe
    50                  55                  60

Lys Gly Lys Ala Thr Leu Thr Val Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Ala Arg Tyr Tyr Tyr Ala Met Asp Tyr Trp Gly Gln Gly Thr Ser Val
            100                 105                 110

Thr Val Ser Ser
        115


<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Asp Tyr Tyr Met Asn
1               5


<210> SEQ ID NO 11
<211> LENGTH: 17
<212> TYPE: PRT
<213> ORGANISM: Artificial Sequence
<220> FEATURE:
<223> OTHER INFORMATION: Synthetic peptide

<400> SEQUENCE: 11

Asn Ile Asn Pro Asn His Asp Tyr Thr Ser Tyr Asn Gln Lys Phe Lys
1               5                   10                  15
```

Gly

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

```
Tyr Tyr Tyr Ala Met Asp Tyr
1               5
```

<210> SEQ ID NO 13
<211> LENGTH: 108
<212> TYPE: PRT
<213> ORGANISM: Mus musculus

<400> SEQUENCE: 13

```
Gln Ile Val Leu Thr Gln Ser Pro Ala Ile Met Ser Ala Phe Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Phe
        35                  40                  45

Asp Thr Ser Thr Leu Ala Ser Gly Val Pro Val Arg Phe Ser Gly Ser
    50                  55                  60

Gly Ser Gly Thr Ser His Ser Leu Thr Ile Ser Arg Met Glu Ala Glu
65                  70                  75                  80

Asp Ala Ala Thr Tyr Tyr Cys Gln Gln Trp Ser Ser Phe Pro Pro Thr
                85                  90                  95

Phe Gly Ala Gly Thr Arg Leu Glu Leu Lys Arg Ala
            100                 105
```

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

```
Ser Ala Ser Ser Ser Val Ser Tyr Met Tyr
1               5                   10
```

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

```
Asp Thr Ser Thr Leu Ala Ser
1               5
```

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Gln Gln Trp Ser Ser Phe Pro Pro Thr
1               5

<210> SEQ ID NO 17
<211> LENGTH: 115
<212> TYPE: PRT
<213> ORGANISM: Mus musculus

<400> SEQUENCE: 17

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp His
            20                  25                  30

Tyr Met Asn Trp Val Lys Gln Ser His Gly Lys Ser Leu Glu Trp Ile
        35                  40                  45

Gly Asp Ile Asp Pro Lys Asn Gly Gly Thr Leu Tyr Asn Gln Asn Phe
    50                  55                  60

Lys Gly Arg Ala Thr Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Arg Glu Ala Met Asp Tyr Trp Gly Gln Gly Thr Ser Val Thr
            100                 105                 110

Val Ser Ser
        115

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide

<400> SEQUENCE: 18

Asp His Tyr Met Asn
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide

<400> SEQUENCE: 19

Asp Ile Asp Pro Lys Asn Gly Gly Thr Leu Tyr Asn Gln Asn Phe Lys
1               5                   10                  15

Gly

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Arg Glu Ala Met Asp Tyr
1               5

<210> SEQ ID NO 21

<211> LENGTH: 114
<212> TYPE: PRT
<213> ORGANISM: Mus musculus

<400> SEQUENCE: 21

Asp Val Leu Met Thr Gln Ile Pro Leu Ser Leu Pro Val Ser Phe Gly
1 5 10 15

Asp Gln Ala Ser Ile Ser Cys Arg Ser Ser Gln Ser Ile Val Tyr Ser
20 25 30

Asn Gly Asn Thr Tyr Leu Asn Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Trp Thr Phe Gly Gly Gly Thr Lys Leu Glu Ile Lys
100 105 110

Arg Ala

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide

<400> SEQUENCE: 22

Arg Ser Ser Gln Ser Ile Val Tyr Ser Asn Gly Asn Thr Tyr Leu Asn
1 5 10 15

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Lys Val Ser Asn Arg Phe Ser
1 5

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Phe Gln Gly Ser His Val Pro Trp Thr
1 5

<210> SEQ ID NO 25
<211> LENGTH: 116
<212> TYPE: PRT
<213> ORGANISM: Mus musculus

<400> SEQUENCE: 25

Glu Val Gln Leu Gln Gln Ser Gly Pro Glu Leu Val Lys Pro Gly Thr
1 5 10 15

Ser Val Lys Ile Ser Cys Lys Ala Ser Gly Tyr Thr Phe Thr Asp His
20 25 30

Tyr Met His Trp Val Arg Gln Ser His Gly Lys Ser Leu Glu Trp Ile
35 40 45

Gly Asp Ile Asn Pro Asn Ser Gly Gly Thr Ile Asn Asn Gln Asn Phe
50 55 60

Lys Gly Lys Ala Thr Leu Thr Val Asp Lys Ser Ser Asn Thr Ala Tyr
65 70 75 80

Met Gly Leu His Ser Leu Thr Ser Glu Asp Ser Ala Val Tyr Tyr Cys
85 90 95

Ala Ser Gly Phe Ser Gly Leu Ala Tyr Trp Gly Gln Gly Thr Leu Val
100 105 110

Thr Val Ser Ala
115

<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Asp His Tyr Met His
1 5

<210> SEQ ID NO 27
<211> LENGTH: 16
<212> TYPE: PRT
<213> ORGANISM: Artificial Sequence
<220> FEATURE:
<223> OTHER INFORMATION: Synthetic peptide

<400> SEQUENCE: 27

Asp Ile Asn Pro Asn Ser Gly Gly Thr Ile Asn Asn Gln Asn Phe Lys
1 5 10 15

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide

<400> SEQUENCE: 28

Gly Phe Ser Gly Leu Ala Tyr
1 5

<210> SEQ ID NO 29
<211> LENGTH: 114
<212> TYPE: PRT
<213> ORGANISM: Mus musculus

<400> SEQUENCE: 29

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Asp Arg
20 25 30

Asp Gly Lys Thr Tyr Leu Asn Trp Leu Phe Gln Arg Pro Gly Gln Ser
35 40 45

Leu Lys Arg Leu Ile Tyr Leu Val Ser Ile Leu Asp Ser Gly Val Pro
50 55 60

```
Asp Arg Phe Thr Gly Ser Gly Ser Gly Thr Asp Phe Thr Leu Lys Ile
65                  70                  75                  80

Ser Arg Val Glu Ala Gly Asp Leu Gly Ile Tyr Tyr Cys Trp Gln Gly
                85                  90                  95

Thr His Phe Pro Trp Thr Phe Gly Gly Gly Thr Lys Leu Glu Ile Lys
            100                 105                 110

Arg Ala


<210> SEQ ID NO 30
<211> LENGTH: 16
<212> TYPE: PRT
<213> ORGANISM: Artificial Sequence
<220> FEATURE:
<223> OTHER INFORMATION: Synthetic peptide

<400> SEQUENCE: 30

Lys Ser Ser Gln Ser Leu Leu Asp Arg Asp Gly Lys Thr Tyr Leu Asn
1               5                   10                  15


<210> SEQ ID NO 31
<211> LENGTH: 7
<212> TYPE: PRT
<213> ORGANISM: Artificial Sequence
<220> FEATURE:
<223> OTHER INFORMATION: Synthetic peptide

<400> SEQUENCE: 31

Leu Val Ser Ile Leu Asp Ser
1               5


<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Trp Gln Gly Thr His Phe Pro Trp Thr
1               5


<210> SEQ ID NO 33
<211> LENGTH: 117
<212> TYPE: PRT
<213> ORGANISM: Mus musculus

<400> SEQUENCE: 33

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Ala Ser Glu Asp Ser Ala Val Tyr Tyr Cys
                85                  90                  95

Ala Arg Phe Glu Gly Arg Gln Phe Ala Tyr Trp Gly Gln Gly Thr Leu
            100                 105                 110
```

Val Thr Val Ser Ala
115

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Ser Tyr Trp Met Gln
1 5

<210> SEQ ID NO 35
<211> LENGTH: 17
<212> TYPE: PRT
<213> ORGANISM: Artificial Sequence
<220> FEATURE:
<223> OTHER INFORMATION: Synthetic peptide

<400> SEQUENCE: 35

Thr Ile Tyr Pro Gly Asp Gly Asp Thr Arg Tyr Thr Gln Lys Phe Lys
1 5 10 15

Gly

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Phe Glu Gly Arg Gln Phe Ala Tyr
1 5

<210> SEQ ID NO 37
<211> LENGTH: 106
<212> TYPE: PRT
<213> ORGANISM: Mus musculus

<400> SEQUENCE: 37

Met Thr Gln Ser Pro Ala Ser Leu Ser Val Ser Val Gly Glu Thr Val
1 5 10 15

Thr Ile Thr Cys Arg Ala Ser Glu Asn Ile Tyr Ser Asn Leu Ala Trp
20 25 30

Tyr Gln Gln Lys Gln Gly Lys Ser Pro Gln Leu Leu Val Tyr Ala Ala
35 40 45

Thr Asn Leu Ala Asp Gly Val Pro Ser Arg Phe Ser Gly Ser Gly Ser
50 55 60

Gly Thr Gln Tyr Ser Leu Lys Ile Asn Ser Leu Gln Ser Glu Asp Phe
65 70 75 80

Gly Ser Tyr Tyr Cys Gln His Phe Trp Gly Pro Pro Trp Thr Phe Gly
85 90 95

Gly Gly Thr Lys Leu Glu Ile Lys Arg Ala
100 105

<210> SEQ ID NO 38
<211> LENGTH: 11
<212> TYPE: PRT
<213> ORGANISM: Artificial Sequence
<220> FEATURE:
<223> OTHER INFORMATION: Synthetic peptide

<400> SEQUENCE: 38

Arg Ala Ser Glu Asn Ile Tyr Ser Asn Leu Ala
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Ala Ala Thr Asn Leu Ala Asp
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide

<400> SEQUENCE: 40

Gln His Phe Trp Gly Pro Pro Trp Thr
1               5

<210> SEQ ID NO 41
<211> LENGTH: 118
<212> TYPE: PRT
<213> ORGANISM: Mus musculus

<400> SEQUENCE: 41

Gln Val Gln Leu Gln Gln Ser Gly Ala Glu Val Met Lys Pro Gly Ala
1               5                   10                  15

Ser Val Lys Ile Ser Cys Lys Ala Thr Asp Tyr Ile Phe Ser Arg Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Tyr Asn Asn Ser Asn Asp Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Phe Glu Asp Ser Ala Val Tyr Tyr Cys
                85                  90                  95

Ala Arg Lys Gly Thr Phe Tyr Thr Met Asp His Trp Gly Gln Gly Thr
            100                 105                 110

Ser Val Thr Val Ser Ser
        115

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Asn Tyr Leu Ile Glu
1               5

<210> SEQ ID NO 43
<211> LENGTH: 17
<212> TYPE: PRT
<213> ORGANISM: Artificial Sequence
<220> FEATURE:
<223> OTHER INFORMATION: Synthetic peptide

<400> SEQUENCE: 43

```
Glu Ile Leu Pro Gly Ser Gly Tyr Asn Asn Ser Asn Asp Lys Phe Lys
1               5                   10                  15

Gly
```

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

```
Lys Gly Thr Phe Tyr Thr Met Asp His
1               5
```

<210> SEQ ID NO 45
<211> LENGTH: 110
<212> TYPE: PRT
<213> ORGANISM: Mus musculus

<400> SEQUENCE: 45

```
Asp Ile Val Met Thr Gln Ser Thr Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Phe His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Arg Gly Ser Gly Thr Ser Tyr Ser Leu Thr Ile Ser Ser Val Glu
65                  70                  75                  80

Ala Glu Asp Ala Ala Thr Tyr Tyr Cys His Gln Tyr His His Ser Pro
                85                  90                  95

Arg Thr Phe Gly Gly Gly Ser Lys Leu Glu Ile Lys Arg Ala
            100                 105                 110
```

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide

<400> SEQUENCE: 46

```
Thr Ala Ser Ser Ser Val Ser Ser Ser Tyr Phe His
1               5                   10
```

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

```
Ser Thr Ser Asn Leu Ala Ser
1               5


<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

His Gln Tyr His His Ser Pro Arg Thr
1               5


<210> SEQ ID NO 49
<211> LENGTH: 117
<212> TYPE: PRT
<213> ORGANISM: Mus musculus

<400> SEQUENCE: 49

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Ile Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Phe Glu Gly Arg Gln Phe Ala Tyr Trp Gly Gln Gly Thr Leu
            100                 105                 110

Val Thr Val Ser Ala
        115


<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Ser Tyr Trp Met Gln
1               5


<210> SEQ ID NO 51
<211> LENGTH: 17
<212> TYPE: PRT
<213> ORGANISM: Artificial Sequence
<220> FEATURE:
<223> OTHER INFORMATION: Synthetic peptide

<400> SEQUENCE: 51

Thr Ile Tyr Pro Gly Asp Gly Asp Thr Arg Tyr Thr Gln Lys Phe Lys
1               5                   10                  15

Gly


<210> SEQ ID NO 52
```

<211> LENGTH: 8
<212> TYPE: PRT
<213> ORGANISM: Artificial Sequence
<220> FEATURE:
<223> OTHER INFORMATION: Synthetic peptide

<400> SEQUENCE: 52

Phe Glu Gly Arg Gln Phe Ala Tyr
1 5

<210> SEQ ID NO 53
<211> LENGTH: 109
<212> TYPE: PRT
<213> ORGANISM: Mus musculus

<400> SEQUENCE: 53

Asp Ile Gln Met Thr Gln Ser Pro Ala Ser Leu Ser Val Ser Val Gly
1 5 10 15

Glu Thr Val Thr Ile Thr Cys Arg Ala Ser Glu Asn Ile Tyr Ser Asn
20 25 30

Leu Ala Trp Tyr Gln Gln Lys Gln Gly Lys Ser Pro Gln Leu Leu Val
35 40 45

Tyr Ala Ala Thr Asn Leu Ala Asp Gly Val Pro Ser Arg Phe Ser Gly
50 55 60

Ser Gly Ser Gly Thr Gln Tyr Ser Leu Lys Ile Asn Ser Leu Gln Ser
65 70 75 80

Glu Asp Phe Gly Ser Tyr Tyr Cys Gln His Phe Trp Gly Pro Pro Trp
85 90 95

Thr Phe Gly Gly Gly Thr Lys Leu Glu Ile Lys Arg Ala
100 105

<210> SEQ ID NO 54
<211> LENGTH: 11
<212> TYPE: PRT
<213> ORGANISM: Artificial Sequence
<220> FEATURE:
<223> OTHER INFORMATION: Synthetic peptide

<400> SEQUENCE: 54

Arg Ala Ser Glu Asn Ile Tyr Ser Asn Leu Ala
1 5 10

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Ala Ala Thr Asn Leu Ala Asp
1 5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gln His Phe Trp Gly Pro Pro Trp Thr
1 5

<210> SEQ ID NO 57
<211> LENGTH: 118
<212> TYPE: PRT
<213> ORGANISM: Mus musculus

<400> SEQUENCE: 57

Glu Val Lys Leu Glu Glu Ser Gly Gly Gly Leu Val Asn Leu Gly Ala
1               5                   10                  15

Ser Val Lys Ile Ser Cys Lys Ala Thr Gly Tyr Pro Val Ser Arg Tyr
            20                  25                  30

Trp Ile Glu Trp Leu Lys Gln Arg Pro Gly His Gly Pro Glu Trp Ile
        35                  40                  45

Gly Glu Ile Leu Pro Gly Ser Asp Tyr Ala Asn Tyr Asn Glu Lys Phe
    50                  55                  60

Lys Gly Lys Ala Thr Phe Thr Ala Asp Ile Ser Ser Asn Ser Ala Tyr
65                  70                  75                  80

Met Gln Leu Ser Ser Leu Thr Ser Glu Asp Ser Ala Val Tyr Tyr Cys
                85                  90                  95

Ser Arg Lys Gly Ala Tyr Tyr Ala Leu Asp Phe Trp Gly Gln Gly Thr
            100                 105                 110

Ser Val Thr Val Ser Ser
        115

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide

<400> SEQUENCE: 58

Arg Tyr Trp Ile Glu
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic peptide

<400> SEQUENCE: 59

Glu Ile Leu Pro Gly Ser Asp Tyr Ala Asn Tyr Asn Glu Lys Phe Lys
1               5                   10                  15

Gly

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Lys Gly Ala Tyr Tyr Ala Leu Asp Phe
1               5

<210> SEQ ID NO 61
<211> LENGTH: 109
<212> TYPE: PRT
<213> ORGANISM: Mus musculus

<400> SEQUENCE: 61

Asp Ile Val Leu Thr Gln Ser Pro Ala Thr Leu Ser Val Thr Pro Gly
1               5                   10                  15

Glu Arg Val Ser Leu Ser Cys Arg Ala Ser Gln Ser Val Asn Asn Tyr
            20                  25                  30

Leu His Trp Tyr Gln Gln Lys Ser His Glu Ser Pro Arg Leu Leu Ile
        35                  40                  45

Ser Tyr Ala Ser Gln Ser Ile Ser Gly Ile Ser Ser Arg Phe Ser Gly
    50                  55                  60

Ser Gly Ser Gly Thr Asp Phe Thr Leu Ile Ile His Ser Val Glu Thr
65                  70                  75                  80

Glu Asp Phe Gly Met Tyr Phe Cys Gln Gln Ser Asn Arg Trp Pro Leu
                85                  90                  95

Thr Phe Gly Ala Gly Thr Lys Leu Glu Leu Lys Arg Ala
            100                 105

<210> SEQ ID NO 62
<211> LENGTH: 11
<212> TYPE: PRT
<213> ORGANISM: Artificial Sequence
<220> FEATURE:
<223> OTHER INFORMATION: Synthetic peptide

<400> SEQUENCE: 62

Arg Ala Ser Gln Ser Val Asn Asn Tyr Leu His
1               5                   10

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Tyr Ala Ser Gln Ser Ile Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Gln Gln Ser Asn Arg Trp Pro Leu Thr
1               5

<210> SEQ ID NO 65
<211> LENGTH: 117
<212> TYPE: PRT
<213> ORGANISM: Mus musculus

<400> SEQUENCE: 65

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

```
Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Val Tyr
65                  70                  75                  80

Met Gln Leu Thr Ser Leu Ala Ser Glu Asp Ser Ala Val Tyr Tyr Cys
                85                  90                  95

Ala Arg Phe Tyr Gly Gly Ala Met Asp Ser Trp Gly Gln Gly Thr Ser
            100                 105                 110

Val Thr Val Ser Ser
        115


<210> SEQ ID NO 66
<211> LENGTH: 5
<212> TYPE: PRT
<213> ORGANISM: Artificial Sequence
<220> FEATURE:
<223> OTHER INFORMATION: Synthetic peptide

<400> SEQUENCE: 66

Ser Tyr Trp Met Gln
1               5


<210> SEQ ID NO 67
<211> LENGTH: 17
<212> TYPE: PRT
<213> ORGANISM: Artificial Sequence
<220> FEATURE:
<223> OTHER INFORMATION: Synthetic peptide

<400> SEQUENCE: 67

Thr Ile Tyr Pro Gly Asp Gly Asp Thr Arg Tyr Thr Gln Lys Phe Lys
1               5                   10                  15

Gly


<210> SEQ ID NO 68
<211> LENGTH: 8
<212> TYPE: PRT
<213> ORGANISM: Artificial Sequence
<220> FEATURE:
<223> OTHER INFORMATION: Synthetic peptide

<400> SEQUENCE: 68

Phe Tyr Gly Gly Ala Met Asp Ser
1               5


<210> SEQ ID NO 69
<211> LENGTH: 109
<212> TYPE: PRT
<213> ORGANISM: Mus musculus

<400> SEQUENCE: 69

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln His Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Gly Gly Ser Gly Thr Gln Tyr Ser Leu Lys Ile Asn Ser Leu Gln Ser
65                  70                  75                  80
```

```
Glu Asp Phe Gly Thr Tyr Tyr Cys Gln His Phe Trp Gly Pro Pro Trp
                85                  90                  95

Thr Phe Gly Gly Gly Thr Lys Leu Glu Ile Lys Arg Ala
            100                 105


<210> SEQ ID NO 70
<211> LENGTH: 11
<212> TYPE: PRT
<213> ORGANISM: Artificial Sequence
<220> FEATURE:
<223> OTHER INFORMATION: Synthetic peptide

<400> SEQUENCE: 70

Arg Ala Ser Glu Asn Ile Tyr Ser Asn Leu Ala
1               5                   10


<210> SEQ ID NO 71
<211> LENGTH: 7
<212> TYPE: PRT
<213> ORGANISM: Artificial Sequence
<220> FEATURE:
<223> OTHER INFORMATION: Synthetic peptide

<400> SEQUENCE: 71

Ala Ala Thr Asn Leu Ala Asp
1               5


<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Gln His Phe Trp Gly Pro Pro Trp Thr
1               5


<210> SEQ ID NO 73
<211> LENGTH: 119
<212> TYPE: PRT
<213> ORGANISM: Mus musculus

<400> SEQUENCE: 73

Glu Val Gln Leu Gln Gln Ser Gly Pro Glu Leu Val Lys Pro Gly Ala
1               5                   10                  15

Ser Val Lys Met Ser Cys Lys Ala Ser Gly Phe Thr Phe Thr Asp Ser
            20                  25                  30

Val Leu His Trp Val Lys Gln Lys Pro Gly Gln Gly Leu Glu Trp Ile
        35                  40                  45

Gly Tyr Ile His Pro Tyr Asn Asp Asp Thr Lys Phe His Asp Ser Phe
    50                  55                  60

Lys Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ser Arg Asn Asp Glu Leu Arg Val Ala Leu Asp Tyr Trp Gly Gln Gly
            100                 105                 110

Thr Ser Val Thr Val Ser Ser
        115


<210> SEQ ID NO 74
```

<211> LENGTH: 5
<212> TYPE: PRT
<213> ORGANISM: Artificial Sequence
<220> FEATURE:
<223> OTHER INFORMATION: Synthetic peptide

<400> SEQUENCE: 74

Asp Ser Val Leu His
1 5

<210> SEQ ID NO 75
<211> LENGTH: 17
<212> TYPE: PRT
<213> ORGANISM: Artificial Sequence
<220> FEATURE:
<223> OTHER INFORMATION: Synthetic peptide

<400> SEQUENCE: 75

Tyr Ile His Pro Tyr Asn Asp Asp Thr Lys Phe His Asp Ser Phe Lys
1 5 10 15

Gly

<210> SEQ ID NO 76
<211> LENGTH: 10
<212> TYPE: PRT
<213> ORGANISM: Artificial Sequence
<220> FEATURE:
<223> OTHER INFORMATION: Synthetic peptide

<400> SEQUENCE: 76

Asn Asp Glu Leu Arg Val Ala Leu Asp Tyr
1 5 10

<210> SEQ ID NO 77
<211> LENGTH: 113
<212> TYPE: PRT
<213> ORGANISM: Mus musculus

<400> SEQUENCE: 77

Asp Ile Val Leu Thr Gln Ser Pro Ala Ser Leu Ala Val Ser Leu Gly
1 5 10 15

Gln Arg Ala Thr Ile Ser Cys Arg Ala Ser Gln Ser Val Ser Thr Ser
20 25 30

Thr Tyr Ser Tyr Val His Trp Tyr Gln Gln Lys Pro Gly Gln Pro Pro
35 40 45

Lys Leu Leu Ile Lys Tyr Ala Ser Asn Leu Glu Ser Gly Val Pro Ala
50 55 60

Arg Phe Ser Gly Arg Gly Ser Gly Thr Asp Phe Thr Leu Ser Ile His
65 70 75 80

Pro Val Glu Gly Glu Asp Ala Ala Thr Tyr Tyr Cys Gln His Ser Trp
85 90 95

Gly Asn Pro Trp Thr Phe Gly Gly Gly Thr Lys Leu Glu Ile Lys Arg
100 105 110

Ala

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide

<400> SEQUENCE: 78

Arg Ala Ser Gln Ser Val Ser Thr Ser Thr Tyr Ser Tyr Val His
1 5 10 15

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Tyr Ala Ser Asn Leu Glu Ser
1 5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Gln His Ser Trp Gly Asn Pro Trp Thr
1 5

<210> SEQ ID NO 81
<211> LENGTH: 115
<212> TYPE: PRT
<213> ORGANISM: Mus musculus

<400> SEQUENCE: 81

Asp Val Gln Leu Gln Glu Ser Gly Pro Gly Leu Val Lys Pro Ser His
1 5 10 15

Ser Leu Ser Leu Thr Cys Thr Val Thr Gly Tyr Ser Ile Thr Ser Asp
20 25 30

Tyr Ala Trp Asn Trp Ile Arg Gln Phe Pro Gly Asn Asn Leu Glu Trp
35 40 45

Met Gly Tyr Ile Thr Tyr Ser Gly Ser Thr Gly Tyr Asn Pro Ser Leu
50 55 60

Lys Ser Arg Ile Ser Ile Thr Arg Asp Thr Ser Lys Asn Gln Phe Phe
65 70 75 80

Leu Gln Leu Asn Ser Val Thr Ala Glu Asp Thr Ala Thr Tyr Tyr Cys
85 90 95

Ala Arg Asp Trp Pro Phe Ala Tyr Trp Gly Gln Gly Thr Leu Val Thr
100 105 110

Val Ser Ala
115

<210> SEQ ID NO 82
<211> LENGTH: 5
<212> TYPE: PRT
<213> ORGANISM: Artificial Sequence
<220> FEATURE:
<223> OTHER INFORMATION: Synthetic peptide

<400> SEQUENCE: 82

Arg Tyr Trp Ile Glu
1 5

<210> SEQ ID NO 83
<211> LENGTH: 17
<212> TYPE: PRT

<213> ORGANISM: Artificial Sequence
<220> FEATURE:
<223> OTHER INFORMATION: Synthetic peptide

<400> SEQUENCE: 83

```
Glu Ile Leu Pro Gly Ser Asp Tyr Ala Asn Tyr Asn Glu Lys Phe Lys
1               5                   10                  15

Gly
```

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

```
Lys Gly Ala Tyr Tyr Ala Leu Asp Phe
1               5
```

<210> SEQ ID NO 85
<211> LENGTH: 108
<212> TYPE: PRT
<213> ORGANISM: Mus musculus

<400> SEQUENCE: 85

```
Gln Ile Val Leu Thr Gln Ser Pro Ala Ile Met Ser Ala Ser Pro Gly
1               5                   10                  15

Glu Lys Ala Thr Ile Thr Cys Ser Ala Ser Ser Ser Val Ser Tyr Met
            20                  25                  30

His Trp Phe Gln Gln Arg Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Phe Ser Leu Thr Ile Ser Arg Met Glu Ala Glu
65                  70                  75                  80

Asp Ala Ala Thr Tyr Tyr Cys His Gln Arg Ser Gly His Thr Phe Thr
                85                  90                  95

Phe Gly Ser Gly Thr Lys Leu Glu Ile Lys Arg Ala
            100                 105
```

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

```
Ser Ala Ser Ser Ser Val Ser Tyr Met His
1               5                   10
```

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide

<400> SEQUENCE: 87

```
Ser Thr Ser Asn Leu Ala Ser
1               5
```

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

His Gln Arg Ser Gly His Thr Phe Thr
1               5

<210> SEQ ID NO 89
<211> LENGTH: 119
<212> TYPE: PRT
<213> ORGANISM: Mus musculus

<400> SEQUENCE: 89

Glu Val Lys Leu Glu Glu Ser Gly Gly Gly Leu Val Gln Pro Gly Gly
1               5                   10                  15

Ser Leu Lys Leu Ser Cys Ala Ala Ser Gly Phe Thr Leu Ser Arg Tyr
            20                  25                  30

Thr Met Ser Trp Val Arg Gln Thr Pro Glu Lys Arg Leu Glu Trp Val
        35                  40                  45

Ala Tyr Ile Ser Asn Gly Gly Gly Ser Thr Tyr Tyr Pro Asp Thr Val
    50                  55                  60

Lys Gly Arg Phe Thr Thr Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Gly Arg Ala Glu Ala Gly Thr Asp Trp Phe Ala Tyr Trp Gly Gln Gly
            100                 105                 110

Thr Leu Val Thr Val Ser Ala
        115

<210> SEQ ID NO 90
<211> LENGTH: 5
<212> TYPE: PRT
<213> ORGANISM: Artificial Sequence
<220> FEATURE:
<223> OTHER INFORMATION: Synthetic peptide

<400> SEQUENCE: 90

Ser Tyr Trp Met Gln
1               5

<210> SEQ ID NO 91
<211> LENGTH: 17
<212> TYPE: PRT
<213> ORGANISM: Artificial Sequence
<220> FEATURE:
<223> OTHER INFORMATION: Synthetic peptide

<400> SEQUENCE: 91

Thr Ile Tyr Pro Gly Asp Gly Asp Thr Arg Tyr Thr Gln Lys Phe Lys
1               5                   10                  15

Gly

<210> SEQ ID NO 92
<211> LENGTH: 8
<212> TYPE: PRT
<213> ORGANISM: Artificial Sequence
<220> FEATURE:

<223> OTHER INFORMATION: Synthetic peptide

<400> SEQUENCE: 92

Phe Tyr Gly Gly Ala Met Asp Ser
1               5

<210> SEQ ID NO 93
<211> LENGTH: 113
<212> TYPE: PRT
<213> ORGANISM: Mus musculus

<400> SEQUENCE: 93

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Gly Trp
                85                  90                  95

Glu Ile Pro Tyr Thr Phe Gly Gly Gly Thr Lys Leu Glu Ile Lys Arg
            100                 105                 110

Ala

<210> SEQ ID NO 94
<211> LENGTH: 15
<212> TYPE: PRT
<213> ORGANISM: Artificial Sequence
<220> FEATURE:
<223> OTHER INFORMATION: Synthetic peptide

<400> SEQUENCE: 94

Arg Ala Ser Gln Ser Val Ser Thr Ser Ser Tyr Ser Tyr Met His
1               5                   10                  15

<210> SEQ ID NO 95
<211> LENGTH: 7
<212> TYPE: PRT
<213> ORGANISM: Artificial Sequence
<220> FEATURE:
<223> OTHER INFORMATION: Synthetic peptide

<400> SEQUENCE: 95

Tyr Ala Ser Asn Leu Glu Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Gln His Gly Trp Glu Ile Pro Tyr Thr
1               5

<210> SEQ ID NO 97

<211> LENGTH: 119
<212> TYPE: PRT
<213> ORGANISM: Mus musculus

<400> SEQUENCE: 97

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Asn
            20                  25                  30

Trp Met Asn Trp Val Lys Gln Arg Pro Gly His Gly Leu Glu Trp Ile
        35                  40                  45

Gly Asn Ile Tyr Pro Ser Asn Gly Gly Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Arg Gly Leu Thr Ser Glu Asp Ser Ala Val Tyr Tyr Cys
                85                  90                  95

Val Arg His Ser Asn Tyr Val Gly Ala Met Asp Tyr Trp Gly Gln Gly
            100                 105                 110

Thr Ser Val Thr Val Ser Ser
        115

<210> SEQ ID NO 98
<211> LENGTH: 5
<212> TYPE: PRT
<213> ORGANISM: Artificial Sequence
<220> FEATURE:
<223> OTHER INFORMATION: Synthetic peptide

<400> SEQUENCE: 98

Ser Asn Trp Met Asn
1               5

<210> SEQ ID NO 99
<211> LENGTH: 17
<212> TYPE: PRT
<213> ORGANISM: Artificial Sequence
<220> FEATURE:
<223> OTHER INFORMATION: Synthetic peptide

<400> SEQUENCE: 99

Asn Ile Tyr Pro Ser Asn Gly Gly Thr Asn Tyr Asn Glu Lys Phe Lys
1               5                   10                  15

Ser

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

His Ser Asn Tyr Val Gly Ala Met Asp Tyr
1               5                   10

<210> SEQ ID NO 101
<211> LENGTH: 108
<212> TYPE: PRT
<213> ORGANISM: Mus musculus

<400> SEQUENCE: 101

```
Gln Ile Val Leu Thr Gln Ser Pro Ala Ile Met Ser Ala Ser Pro Gly
1               5                   10                  15

Glu Lys Val Thr Met Thr Cys Gly Ala Ser Ser Ser Val Ser Tyr Met
            20                  25                  30

Tyr Trp Phe Gln Gln Lys Pro Gly Ser Ser Pro Arg Leu Leu Ile Tyr
        35                  40                  45

Asp Thr Phe Asn Leu Ala Ser Gly Val Pro Val Arg Phe Ser Gly Ser
    50                  55                  60

Glu Ser Gly Thr Ser Tyr Ser Leu Thr Ile Ser Arg Met Glu Ala Glu
65                  70                  75                  80

Asp Ala Ala Thr Tyr Tyr Cys Gln His Trp Ser Ser Tyr Pro Pro Thr
                85                  90                  95

Phe Gly Ser Gly Thr Lys Leu Glu Ile Asp Arg Ala
            100                 105


<210> SEQ ID NO 102
<211> LENGTH: 10
<212> TYPE: PRT
<213> ORGANISM: Artificial Sequence
<220> FEATURE:
<223> OTHER INFORMATION: Synthetic peptide

<400> SEQUENCE: 102

Gly Ala Ser Ser Ser Val Ser Tyr Met Tyr
1               5                   10


<210> SEQ ID NO 103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 103

Asp Thr Phe Asn Leu Ala Ser
1               5


<210> SEQ ID NO 104
<211> LENGTH: 9
<212> TYPE: PRT
<213> ORGANISM: Artificial Sequence
<220> FEATURE:
<223> OTHER INFORMATION: Synthetic peptide

<400> SEQUENCE: 104

Gln His Trp Ser Ser Tyr Pro Pro Thr
1               5


<210> SEQ ID NO 105
<211> LENGTH: 118
<212> TYPE: PRT
<213> ORGANISM: Mus musculus

<400> SEQUENCE: 105

Gln Val Gln Leu Gln Gln Ser Gly Ala Glu Leu Met Asn Leu Gly Ala
1               5                   10                  15

Ser Val Lys Ile Ser Cys Lys Ala Thr Gly Tyr Pro Val Ser Arg Tyr
            20                  25                  30

Trp Ile Glu Trp Leu Lys Gln Arg Pro Gly His Gly Pro Glu Trp Ile
        35                  40                  45

Gly Glu Ile Leu Pro Gly Ser Asp Tyr Ala Asn Tyr Asn Glu Lys Phe
    50                  55                  60
```

Lys Gly Lys Ala Thr Phe Thr Ala Asp Ile Ser Ser Asn Ser Ala Tyr
65 70 75 80

Met Gln Leu Ser Ser Leu Thr Ser Glu Asp Ser Ala Val Tyr Tyr Cys
85 90 95

Ser Arg Lys Gly Ala Tyr Tyr Ala Leu Asp Phe Trp Gly Gln Gly Thr
100 105 110

Ser Val Thr Val Ser Ser
115

<210> SEQ ID NO 106
<211> LENGTH: 5
<212> TYPE: PRT
<213> ORGANISM: Artificial Sequence
<220> FEATURE:
<223> OTHER INFORMATION: Synthetic peptide

<400> SEQUENCE: 106

Arg Tyr Trp Ile Glu
1 5

<210> SEQ ID NO 107
<211> LENGTH: 17
<212> TYPE: PRT
<213> ORGANISM: Artificial Sequence
<220> FEATURE:
<223> OTHER INFORMATION: Synthetic peptide

<400> SEQUENCE: 107

Glu Ile Leu Pro Gly Ser Asp Tyr Ala Asn Tyr Asn Glu Lys Phe Lys
1 5 10 15

Gly

<210> SEQ ID NO 108
<211> LENGTH: 9
<212> TYPE: PRT
<213> ORGANISM: Artificial Sequence
<220> FEATURE:
<223> OTHER INFORMATION: Synthetic peptide

<400> SEQUENCE: 108

Lys Gly Ala Tyr Tyr Ala Leu Asp Phe
1 5

<210> SEQ ID NO 109
<211> LENGTH: 107
<212> TYPE: PRT
<213> ORGANISM: Mus musculus

<400> SEQUENCE: 109

Asp Ile Val Met Thr Gln Ser Pro Ala Thr Leu Ser Val Thr Pro Gly
1 5 10 15

Glu Arg Val Ser Leu Ser Cys Arg Ala Ser Gln Ser Val Asn Asn Tyr
20 25 30

Leu His Trp Tyr Gln Gln Lys Ser His Glu Ser Pro Arg Leu Leu Ile
35 40 45

Ser Tyr Val Ser Gln Ser Ile Ser Gly Ile Ser Ser Arg Phe Ser Gly
50 55 60

Ser Gly Ser Gly Thr Asp Phe Thr Leu Ile Ile His Ser Val Glu Thr
65 70 75 80

Glu Asp Phe Gly Met Tyr Phe Cys Gln Gln Ser Asn Arg Trp Pro Leu
85 90 95

Thr Phe Gly Ala Gly Thr Lys Leu Glu Leu Lys
            100                 105

<210> SEQ ID NO 110
<211> LENGTH: 11
<212> TYPE: PRT
<213> ORGANISM: Artificial Sequence
<220> FEATURE:
<223> OTHER INFORMATION: Synthetic peptide

<400> SEQUENCE: 110

Arg Ala Ser Gln Ser Val Asn Asn Tyr Leu His
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 111

Tyr Val Ser Gln Ser Ile Ser
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic peptide

<400> SEQUENCE: 112

Gln Gln Ser Asn Arg Trp Pro Leu Thr
1               5

<210> SEQ ID NO 113
<211> LENGTH: 115
<212> TYPE: PRT
<213> ORGANISM: Artificial Sequence
<220> FEATURE:
<223> OTHER INFORMATION: Synthetic peptide

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Tyr Met Asn Trp Val Arg Gln Ala Pro Gly Gln Gly Leu Glu Trp Ile
        35                  40                  45

Gly Asp Ile Asp Pro Lys Asn Gly Gly Thr Leu Tyr Asn Gln Asn Phe
    50                  55                  60

Lys Gly Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Glu Ala Met Asp Tyr Trp Gly Gln Gly Thr Leu Val Thr
            100                 105                 110

Val Ser Ser
        115

<210> SEQ ID NO 114

<211> LENGTH: 112
<212> TYPE: PRT
<213> ORGANISM: Artificial Sequence
<220> FEATURE:
<223> OTHER INFORMATION: Synthetic peptide

<400> SEQUENCE: 114

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Ile Val Tyr Ser
20 25 30

Asn Gly Asn Thr Tyr Leu Asn Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Phe Gln Gly
85 90 95

Ser His Val Pro Trp Thr Phe Gly Gly Gly Thr Lys Val Glu Ile Lys
100 105 110

<210> SEQ ID NO 115
<211> LENGTH: 119
<212> TYPE: PRT
<213> ORGANISM: Artificial Sequence
<220> FEATURE:
<223> OTHER INFORMATION: Synthetic peptide

<400> SEQUENCE: 115

Glu Val Gln Leu Val Gln Ser Gly Ala Glu Val Lys Lys Pro Gly Ala
1 5 10 15

Ser Val Lys Val Ser Cys Lys Ala Ser Gly Phe Thr Phe Thr Asp Ser
20 25 30

Val Leu His Trp Val Arg Gln Ala Pro Gly Gln Arg Leu Glu Trp Ile
35 40 45

Gly Tyr Ile His Pro Tyr Asn Asp Asp Thr Lys Phe His Asp Ser Phe
50 55 60

Lys Gly Arg Ala Thr Leu Thr Ser Asp Lys Ser Ala Ser Thr Ala Tyr
65 70 75 80

Met Glu Leu Ser Ser Leu Arg Ser Glu Asp Thr Ala Val Tyr Tyr Cys
85 90 95

Ser Arg Asn Asp Glu Leu Arg Val Ala Leu Asp Tyr Trp Gly Gln Gly
100 105 110

Thr Leu Val Thr Val Ser Ser
115

<210> SEQ ID NO 116
<211> LENGTH: 111
<212> TYPE: PRT
<213> ORGANISM: Artificial Sequence
<220> FEATURE:
<223> OTHER INFORMATION: Synthetic peptide

<400> SEQUENCE: 116

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Thr Ser
20 25 30

```
Thr Tyr Ser Tyr Val His Trp Tyr Gln Gln Lys Pro Gly Gln Ala Pro
        35                  40                  45

Arg Leu Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Trp
                85                  90                  95

Gly Asn Pro Trp Thr Phe Gly Gly Gly Thr Lys Val Glu Ile Lys
            100                 105                 110


<210> SEQ ID NO 117
<211> LENGTH: 116
<212> TYPE: PRT
<213> ORGANISM: Artificial Sequence
<220> FEATURE:
<223> OTHER INFORMATION: Synthetic peptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Tyr Met His Trp Val Arg Gln Ala Pro Gly Gln Gly Leu Glu Trp Ile
        35                  40                  45

Gly Asp Ile Asn Pro Asn Ser Gly Gly Thr Ile Asn Asn Gln Asn Phe
    50                  55                  60

Lys Gly Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Phe Ser Gly Leu Ala Tyr Trp Gly Gln Gly Thr Leu Val
            100                 105                 110

Thr Val Ser Ser
        115


<210> SEQ ID NO 118
<211> LENGTH: 112
<212> TYPE: PRT
<213> ORGANISM: Artificial Sequence
<220> FEATURE:
<223> OTHER INFORMATION: Synthetic peptide

<400> SEQUENCE: 118

Asp Ile Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Asp Arg
            20                  25                  30

Asp Gly Lys Thr Tyr Leu Asn Trp Leu Gln Gln Arg Pro Gly Gln Pro
        35                  40                  45

Pro Arg Arg Leu Ile Tyr Leu Val Ser Ile Leu Asp Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110
```

<210> SEQ ID NO 119
<211> LENGTH: 118
<212> TYPE: PRT
<213> ORGANISM: Artificial Sequence
<220> FEATURE:
<223> OTHER INFORMATION: Synthetic peptide

<400> SEQUENCE: 119

Glu Val Gln Leu Val Gln Ser Gly Ala Glu Val Lys Lys Pro Gly Glu
1 5 10 15

Ser Leu Arg Ile Ser Cys Lys Gly Ser Gly Tyr Pro Val Ser Arg Tyr
20 25 30

Trp Ile Glu Trp Val Arg Gln Met Pro Gly Lys Gly Leu Glu Trp Ile
35 40 45

Gly Glu Ile Leu Pro Gly Ser Asp Tyr Ala Asn Tyr Asn Glu Lys Phe
50 55 60

Lys Gly His Ala Thr Phe Ser Ala Asp Ile Ser Ile Ser Thr Ala Tyr
65 70 75 80

Leu Gln Trp Ser Ser Leu Lys Ala Ser Asp Thr Ala Met Tyr Tyr Cys
85 90 95

Ser Arg Lys Gly Ala Tyr Tyr Ala Leu Asp Phe Trp Gly Gln Gly Thr
100 105 110

Leu Val Thr Val Ser Ser
115

<210> SEQ ID NO 120
<211> LENGTH: 107
<212> TYPE: PRT
<213> ORGANISM: Artificial Sequence
<220> FEATURE:
<223> OTHER INFORMATION: Synthetic peptide

<400> SEQUENCE: 120

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Asn Asn Tyr
20 25 30

Leu His Trp Tyr Gln Gln Lys Pro Gly Gln Ala Pro Arg Leu Leu Ile
35 40 45

Ser Tyr Ala Ser Gln Ser Ile Ser Gly Ile Pro Ala Arg Phe Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Ser Asn Arg Trp Pro Leu
85 90 95

Thr Phe Gly Gln Gly Thr Lys Leu Glu Ile Lys
100 105

<210> SEQ ID NO 121
<211> LENGTH: 445
<212> TYPE: PRT
<213> ORGANISM: Artificial Sequence
<220> FEATURE:
<223> OTHER INFORMATION: Synthetic peptide

<400> SEQUENCE: 121

Gln Val Gln Leu Val Gln Ser Gly Ala Glu Val Lys Lys Pro Gly Ala
1 5 10 15

-continued

```
Ser Val Lys Val Ser Cys Lys Ala Ser Gly Tyr Thr Phe Thr Asp His
            20                  25                  30

Tyr Met Asn Trp Val Arg Gln Ala Pro Gly Gln Gly Leu Glu Trp Ile
        35                  40                  45

Gly Asp Ile Asp Pro Lys Asn Gly Gly Thr Leu Tyr Asn Gln Asn Phe
    50                  55                  60

Lys Gly Arg Ala Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Glu Ala Met Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
```

435 440 445

<210> SEQ ID NO 122
<211> LENGTH: 219
<212> TYPE: PRT
<213> ORGANISM: Artificial Sequence
<220> FEATURE:
<223> OTHER INFORMATION: Synthetic peptide

<400> SEQUENCE: 122

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val Tyr Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 123
<211> LENGTH: 449
<212> TYPE: PRT
<213> ORGANISM: Artificial Sequence
<220> FEATURE:
<223> OTHER INFORMATION: Synthetic peptide

<400> SEQUENCE: 123

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Asp Ser
            20                  25                  30

Val Leu His Trp Val Arg Gln Ala Pro Gly Gln Arg Leu Glu Trp Ile
        35                  40                  45

Gly Tyr Ile His Pro Tyr Asn Asp Asp Thr Lys Phe His Asp Ser Phe
    50                  55                  60

Lys Gly Arg Ala Thr Leu Thr Ser Asp Lys Ser Ala Ser Thr Ala Tyr
65                  70                  75                  80
```

```
Met Glu Leu Ser Ser Leu Arg Ser Glu Asp Thr Ala Val Tyr Tyr Cys
                85                  90                  95

Ser Arg Asn Asp Glu Leu Arg Val Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 124
<211> LENGTH: 218
<212> TYPE: PRT
<213> ORGANISM: Artificial Sequence
<220> FEATURE:
<223> OTHER INFORMATION: Synthetic peptide

<400> SEQUENCE: 124

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Thr Ser
20 25 30

Thr Tyr Ser Tyr Val His Trp Tyr Gln Gln Lys Pro Gly Gln Ala Pro
35 40 45

Arg Leu Leu Ile Lys Tyr Ala Ser Asn Leu Glu Ser Gly Ile Pro Ala
50 55 60

Arg Phe Ser Gly Ser Gly Ser Gly Thr Asp Phe Thr Leu Thr Ile Ser
65 70 75 80

Ser Leu Glu Pro Glu Asp Phe Ala Val Tyr Tyr Cys Gln His Ser Trp
85 90 95

Gly Asn Pro Trp Thr Phe Gly Gly Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 125
<211> LENGTH: 442
<212> TYPE: PRT
<213> ORGANISM: Artificial Sequence
<220> FEATURE:
<223> OTHER INFORMATION: Synthetic peptide

<400> SEQUENCE: 125

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp His
20 25 30

Tyr Met His Trp Val Arg Gln Ala Pro Gly Gln Gly Leu Glu Trp Ile
35 40 45

Gly Asp Ile Asn Pro Asn Ser Gly Gly Thr Ile Asn Asn Gln Asn Phe
50 55 60

Lys Gly Arg Ala Thr Leu Thr Val Asp Lys Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Phe Ser Gly Leu Ala Tyr Trp Gly Gln Gly Thr Leu Val
100 105 110

Thr Val Ser Ser Ala Ser Thr Lys Gly Pro Ser Val Phe Pro Leu Ala
115 120 125

Pro Cys Ser Arg Ser Thr Ser Glu Ser Thr Ala Ala Leu Gly Cys Leu

```
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440
```

<210> SEQ ID NO 126
<211> LENGTH: 219
<212> TYPE: PRT
<213> ORGANISM: Artificial Sequence
<220> FEATURE:
<223> OTHER INFORMATION: Synthetic peptide

<400> SEQUENCE: 126

```
Asp Ile Val Met Thr Gln Thr Pro Leu Ser Ser Pro Val Thr Leu Gly
1               5                   10                  15

Gln Pro Ala Ser Ile Ser Cys Lys Ser Ser Gln Ser Leu Leu Asp Arg
            20                  25                  30

Asp Gly Lys Thr Tyr Leu Asn Trp Leu Gln Gln Arg Pro Gly Gln Pro
        35                  40                  45

Pro Arg Arg Leu Ile Tyr Leu Val Ser Ile Leu Asp Ser Gly Val Pro
```

```
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 127
<211> LENGTH: 448
<212> TYPE: PRT
<213> ORGANISM: Artificial Sequence
<220> FEATURE:
<223> OTHER INFORMATION: Synthetic peptide

<400> SEQUENCE: 127

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Pro Val Ser Arg Tyr
            20                  25                  30

Trp Ile Glu Trp Val Arg Gln Met Pro Gly Lys Gly Leu Glu Trp Ile
        35                  40                  45

Gly Glu Ile Leu Pro Gly Ser Asp Tyr Ala Asn Tyr Asn Glu Lys Phe
    50                  55                  60

Lys Gly His Ala Thr Phe Ser Ala Asp Ile Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ser Arg Lys Gly Ala Tyr Tyr Ala Leu Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 128
<211> LENGTH: 448
<212> TYPE: PRT
<213> ORGANISM: Artificial Sequence
<220> FEATURE:
<223> OTHER INFORMATION: Synthetic peptide

<400> SEQUENCE: 128

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Pro Val Ser Arg Tyr
            20                  25                  30

Trp Ile Glu Trp Val Arg Gln Met Pro Gly Lys Gly Leu Glu Trp Ile
        35                  40                  45

Gly Glu Ile Leu Pro Gly Ser Asp Tyr Ala Asn Tyr Asn Glu Lys Phe
    50                  55                  60

Lys Gly His Val Thr Phe Ser Ala Asp Ile Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ser Arg Lys Gly Ala Tyr Tyr Ala Leu Asp Phe Trp Gly Gln Gly Thr
            100                 105                 110

Leu Val Thr Val Ser Ser Ala Ser Thr Lys Gly Pro Ser Val Phe Pro
```

```
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 129
<211> LENGTH: 447
<212> TYPE: PRT
<213> ORGANISM: Artificial Sequence
<220> FEATURE:
<223> OTHER INFORMATION: Synthetic peptide

<400> SEQUENCE: 129

Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Pro Val Ser Arg Tyr
            20                  25                  30

Trp Ile Glu Trp Val Arg Gln Met Pro Gly Lys Gly Leu Glu Trp Ile
```

```
        35                  40                  45

Gly Glu Ile Leu Pro Gly Ser Asp Tyr Ala Asn Tyr Asn Glu Lys Phe
    50                  55                  60

Lys Gly His Val Thr Phe Ser Ala Asp Ile Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ser Arg Lys Gly Ala Tyr Tyr Ala Leu Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ala Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Ala Ala Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445
```

<210> SEQ ID NO 130

<211> LENGTH: 444
<212> TYPE: PRT
<213> ORGANISM: Artificial Sequence
<220> FEATURE:
<223> OTHER INFORMATION: Synthetic peptide

<400> SEQUENCE: 130

```
Glu Val Gln Leu Val Gln Ser Gly Ala Glu Val Lys Lys Pro Gly Glu
1               5                   10                  15

Ser Leu Arg Ile Ser Cys Lys Ala Ser Gly Tyr Pro Val Ser Arg Tyr
            20                  25                  30

Trp Ile Glu Trp Val Arg Gln Met Pro Gly Lys Gly Leu Glu Trp Ile
        35                  40                  45

Gly Glu Ile Leu Pro Gly Ser Asp Tyr Ala Asn Tyr Asn Glu Lys Phe
    50                  55                  60

Lys Gly His Val Thr Phe Ser Ala Asp Ile Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ser Arg Lys Gly Ala Tyr Tyr Ala Leu Asp Phe Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

-continued

```
Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440


<210> SEQ ID NO 131
<211> LENGTH: 214
<212> TYPE: PRT
<213> ORGANISM: Artificial Sequence
<220> FEATURE:
<223> OTHER INFORMATION: Synthetic peptide

<400> SEQUENCE: 131

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Asn Tyr
            20                  25                  30

Leu His Trp Tyr Gln Gln Lys Pro Gly Gln Ala Pro Arg Leu Leu Ile
        35                  40                  45

Ser Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Arg Trp Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```